(12) United States Patent
Berzinis et al.

(10) Patent No.: US 9,815,031 B2
(45) Date of Patent: Nov. 14, 2017

(54) POROUS MEMBRANES AND ASSOCIATED SEPARATION MODULES AND METHODS

(71) Applicant: SABIC Global Technologies B.V., Bergen op Zoom (NL)

(72) Inventors: Albin Peter Berzinis, Delmar, NY (US); Joris de Grooth, Enschede (NL); Johannes de Brouwer, Oisterwijk (NL); Meijuan Zhou, Selkirk, NY (US); Pooja Bajaj, Selkirk, NY (US); Rachel Elizabeth Halbfinger, Glenville, NY (US); Kristi Jean Narang, Selkirk, NY (US)

(73) Assignee: SABIC GLOBAL TECHNOLOGIES B.V., Bergen Op Zoom (NL)

( * ) Notice: Subject to any disclaimer, the term of this patent is extended or adjusted under 35 U.S.C. 154(b) by 0 days.

(21) Appl. No.: 15/356,854

(22) Filed: Nov. 21, 2016

(65) Prior Publication Data
US 2017/0282131 A1 Oct. 5, 2017

Related U.S. Application Data

(60) Provisional application No. 62/314,448, filed on Mar. 29, 2016.

(51) Int. Cl.
*B01D 71/52* (2006.01)
*B01D 71/80* (2006.01)
(Continued)

(52) U.S. Cl.
CPC ........... *B01D 71/52* (2013.01); *A61M 1/1698* (2013.01); *B01D 17/02* (2013.01); *B01D 61/243* (2013.01);
(Continued)

(58) Field of Classification Search
CPC ........ B01D 71/26; B01D 71/38; B01D 71/52; B01D 71/76; B01D 71/80; B01D 61/24;
(Continued)

(56) References Cited

U.S. PATENT DOCUMENTS

| 3,446,856 A | 3/1969 | Hamilton |
| 3,703,564 A | 11/1972 | White |

(Continued)

FOREIGN PATENT DOCUMENTS

| CN | 103007787 A | 4/2013 |
| CN | 103170259 B | 12/2014 |

(Continued)

OTHER PUBLICATIONS

Asatekin et al.; "Anti-fouling ultrafiltration membranes containing polyacrylonitrile-graft-poly(ethylene oxide) comb copolymer additives"; Journal of Membrane Science 298 (2007) pp. 136-146.

(Continued)

*Primary Examiner* — Joseph Drodge
(74) *Attorney, Agent, or Firm* — Cantor Colburn LLP

(57) ABSTRACT

A separation module that includes a porous membrane, where the porous membrane includes a poly(phenylene ether) copolymer containing 10 to 40 mole percent repeat units derived from 2-methyl-6-phenylphenol and 60 to 90 mole percent repeat units derived from 2,6-dimethylphenol; and a block copolymer containing backbone or pendant blocks of poly($C_{2-4}$ alkylene oxide). The separation module can be used in devices for wastewater treatment, water purification, desalination, separating water-insoluble oil from oil-containing wastewater, membrane distillation, sugar purification, protein concentration, enzyme recovery, dialysis, liver dialysis, or blood oxygenation.

25 Claims, 12 Drawing Sheets

(51) Int. Cl.
| | |
|---|---|
| *B01D 69/06* | (2006.01) |
| *B01D 63/10* | (2006.01) |
| *B01D 69/04* | (2006.01) |
| *B01D 69/08* | (2006.01) |
| *B01D 61/36* | (2006.01) |
| *B01D 17/02* | (2006.01) |
| *B01D 61/24* | (2006.01) |
| *B01D 61/32* | (2006.01) |
| *A61M 1/16* | (2006.01) |

(52) U.S. Cl.
CPC .......... *B01D 61/32* (2013.01); *B01D 61/364* (2013.01); *B01D 63/10* (2013.01); *B01D 69/04* (2013.01); *B01D 69/06* (2013.01); *B01D 69/08* (2013.01); *B01D 71/80* (2013.01)

(58) Field of Classification Search
CPC ...... B01D 61/243; B01D 61/32; B01D 63/02; B01D 63/04; B01D 63/06; B01D 63/10; B01D 69/04; B01D 69/08; B01D 69/06; B01D 69/36; B01D 69/364; B01D 17/02; B01D 61/28; B01D 63/08; B01D 63/082; A61M 1/16; A61M 1/1601; A61M 1/1621; A61M 1/1698; A61M 2205/33; A61M 2205/35; A61M 2205/3523; A61M 2205/3546; A61M 2205/3553; A61M 2205/3576; A61M 2205/3592; A61M 2205/50; A61M 2205/502; A61M 2205/52; A61M 2205/60; A61M 2205/6009

USPC .............. 210/321.61, 321.78, 321.79, 321.8, 210/321.87, 321.88, 500.27, 500.28, 210/500.36, 646, 650, 651; 604/4.01, 604/5.01, 6.01, 6.09

See application file for complete search history.

(56) References Cited

U.S. PATENT DOCUMENTS

| | | | |
|---|---|---|---|
| 4,201,880 A | 5/1980 | Van Sorge | |
| 4,277,344 A | 7/1981 | Cadotte | |
| 4,454,284 A | 6/1984 | Ueno et al. | |
| 4,622,206 A | 11/1986 | Torgeson | |
| 4,882,168 A | 11/1989 | Casey et al. | |
| 4,944,775 A | 7/1990 | Hayes | |
| 5,118,327 A | 6/1992 | Nelson et al. | |
| 5,132,363 A | 7/1992 | Furuta et al. | |
| 5,159,027 A | 10/1992 | Kanayama et al. | |
| 5,209,849 A | 5/1993 | Hu et al. | |
| 5,282,964 A | 2/1994 | Young et al. | |
| 5,480,552 A * | 1/1996 | Soltys ............... | B01D 61/147 210/500.23 |
| 5,527,467 A | 6/1996 | Oftshun et al. | |
| 5,527,469 A * | 6/1996 | Lawhorne .......... | C01G 23/0475 210/710 |
| 6,294,499 B1 | 9/2001 | Watson et al. | |
| 6,472,499 B1 | 10/2002 | Braat et al. | |
| 7,166,148 B2 | 1/2007 | Lyons et al. | |
| 7,208,438 B2 | 4/2007 | Ingelbrecht et al. | |
| 8,287,735 B2 | 10/2012 | Hanemaaijer et al. | |
| 8,302,781 B2 | 11/2012 | Wechs et al. | |
| 8,505,745 B2 | 8/2013 | Mayes et al. | |
| 8,769,625 B2 * | 7/2014 | Wang ................ | G06F 19/3418 709/217 |
| 2004/0145127 A1 | 7/2004 | Pinto | |
| 2004/0149127 A1 | 8/2004 | Lyons et al. | |
| 2004/0231663 A1 | 11/2004 | Carter et al. | |
| 2005/0218057 A1 | 10/2005 | Ngee | |
| 2006/0076884 A1 | 4/2006 | Ahn | |
| 2006/0076885 A1 | 4/2006 | Kim et al. | |
| 2006/0137522 A1 | 6/2006 | Nishimura et al. | |
| 2007/0068871 A1 | 3/2007 | Flynn | |
| 2007/0202374 A1 | 8/2007 | Bridges et al. | |
| 2008/0076884 A1 | 3/2008 | Yeager et al. | |
| 2008/0085989 A1 | 4/2008 | Yeager et al. | |
| 2008/0203012 A1 * | 8/2008 | Yeager ................ | B01D 61/025 210/500.36 |
| 2008/0207822 A1 * | 8/2008 | Yeager ................. | C08G 65/44 524/543 |
| 2008/0312349 A1 | 12/2008 | Yeager et al. | |
| 2010/0244306 A1 | 9/2010 | Tang | |
| 2012/0103904 A1 | 5/2012 | Morita et al. | |
| 2012/0277347 A1 | 11/2012 | Bedner et al. | |
| 2012/0305486 A1 | 12/2012 | Storr et al. | |
| 2013/0133036 A1 * | 5/2013 | Wang ................. | G06F 19/3418 726/4 |
| 2013/0220924 A1 | 8/2013 | Maeda | |
| 2016/0008528 A1 | 1/2016 | Roy et al. | |
| 2016/0021191 A1 | 1/2016 | Wang et al. | |
| 2016/0022892 A1 | 1/2016 | Eifler et al. | |
| 2017/0021310 A1 * | 1/2017 | Berzinis ............. | B01D 67/0016 |
| 2017/0036169 A1 * | 2/2017 | Berzinis ............... | B01D 61/145 |
| 2017/0037177 A1 * | 2/2017 | Berzinis ............... | C08F 283/08 |
| 2017/0043297 A1 * | 2/2017 | Berzinis ............... | B01D 61/145 |
| 2017/0043301 A1 * | 2/2017 | Berzinis ............. | B01D 67/0016 |

FOREIGN PATENT DOCUMENTS

| | | |
|---|---|---|
| EP | 0568045 A1 | 11/1993 |
| EP | 0083489 B1 | 4/1999 |
| EP | 1918019 A1 | 5/2008 |
| EP | 2535101 A1 | 12/2012 |
| JP | S60114323 A | 6/1985 |
| JP | 2004231743 A | 8/2004 |
| WO | 0240140 A1 | 5/2002 |
| WO | 03000389 A2 | 1/2003 |
| WO | 2004056459 A1 | 7/2004 |
| WO | 2005107929 A2 | 11/2005 |
| WO | WO 2008036454 A1 | 3/2008 |
| WO | 2008103599 A2 | 8/2008 |
| WO | 2012008837 A2 | 1/2012 |
| WO | 2013131848 A1 | 9/2013 |
| WO | 2014195234 A1 | 12/2014 |
| WO | 2015168392 A1 | 11/2015 |
| WO | 2015168409 A1 | 11/2015 |
| WO | 2015168414 A1 | 11/2015 |
| WO | 2015168423 A1 | 11/2015 |
| WO | 2015168584 A1 | 11/2015 |
| WO | 2015168592 A1 | 11/2015 |
| WO | 2015168418 A1 | 11/2016 |
| WO | 2016178835 A1 | 11/2016 |

OTHER PUBLICATIONS

ATRP Solutions; 2011 Catalog; 9 pages.

Baker; "Membranes and Modules"; Membrane Technology & Applications, Third Edition; 2012 John Wiley & Sons; pp. 97-178.

Bernardo et al.; "Membrane Gas Separation: A Review/State of the Art"; Ind. Eng. Chem. Res. 2009, 48, pp. 4638-4663.

Chung et al.; "Formation of ultrathin high-performance polyethersulfone hollow-fiber membranes"; Journal of Membrane Science 133 (1997) pp. 161-175.

Cooper et al.; "Preparation and Properties of Poly(arylene oxide) Copolymers"; Advances in Chemistry; American Chemical Society; 1973; pp. 230-257.

Cooper et al.; "Preparation and Properties of Polyarylene Oxide Copolymers"; 1973; pp. 551-556.

Dongliang et al.; "Polyethersulfone hollow fiber gas separation membranes prepared from NMP/alcohol solvent systems"; Journal of Membrane Science; 115; 1996, pp. 85-108.

Kang et al.; "Protein antifouling mechanisms of PAN UF membranes incorporating PAN-g-PEO additive"; Journal of Membrane Science 296 (2007) pp. 42-50.

Kim et al.; "Ultrafiltration membranes prepared from blends of polyethersulfone and poly(1-vinylpyrrolidone-co-styrene) copolymers"; Journal of Membrane Science 262 (2005) pp. 60-68.

(56) References Cited

OTHER PUBLICATIONS

Liang et al.; "Synthesis and characterization of poly(phenylene oxide) graft copolymers by atom transfer radical polymerizations"; European Polymer Journal 45 (2009) pp. 2348-2357.
Petersen; "Composite reverse osmosis and nanofiltration membranes"; Journal of Membrane Science, 83 (1993) pp. 81-150.
Semsarzadeh et al.; "Synthesis and Characterization of Poly(phenylene oxide)-Based Block Copolymers via Cobalt Mediated Radical Polymerization (CMRP)"; Silicon; 6, 2014, pp. 27-34.
Smid et al.; "The formation of asymmetric hollow fibre membranes for gas separation, using PPE of different intrinsic viscosities"; Journal of Membrane Science, 64, 1991, pp. 121-128.
Ulbricht, "Advanced functional polymer membranes", Polymer; 47; Jan. 2006; pp. 2217-2262.
Vandezande et al.; "High throughput study of phase inversion parameters for polyimide-based SRNF membranes"; Journal of Membrane Science, 330, 2009, pp. 307-318.
Wang et al.; "Highly permeable polyethersulfone hollow fiber gas separation membranes prepared using water as non-solvent additive"; Journal of Membrane Science 176 (2000) pp. 147-158.
Wang et al.; "Polyethersulfone hollow fiber gas separation membranes prepared from NMP/alcohol solvent systems"; Journal of Membrane Science 115 (1996) pp. 85-108.
Yang et al.; "Tailoring pore size and pore size distribution of kidney dialysis hollow fiber membranes via dual-bath coagulation approach"; Journal of Membrane Science 290 (2007) pp. 153-163.
Yeager et al.; "Polyethers, Aromatic"; Encyclopedia of Polymer Science and Technology; vol. 11; John Wiley & Sons; pp. 64-87; No Date.
CN 103170259; Machine Translation; Date of Publication: Dec. 10, 2014; 10 pages.
Final Office Action dated Jun. 7, 2017; U.S. Appl. No. 15/356,836, filed Nov. 21, 2016; 16 pages.
International Search Report for International Application No. PCT/US2016/028951; International Filing Date April 22, 2016; dated Jul. 29, 2016; 7 pages.
International Search Report for International Application No. PCT/US2017/022061; Date of Filing: Mar. 13, 2017; dated Jul. 4, 2017; 6 pages.
International Search Report for International Application No. PCT/US2017/022088; Date of Filing: Mar. 13, 2017; dated Jun. 28, 2017; 6 pages.
JP S60114323; Machine Translation; Date of Publication: Jun. 20, 1985; 8 pages.
Loh et al.; "Fabrication of high performance polyethersulfone UF hollow fiber membranes using amphiphilic Pluronic block copolymers as pore-forming additives", J. Membr. Sci., vol. 380; 2011; 114-123.
Non-Final Office Action dated Feb. 16, 2017; U.S. Appl. No. 15/356,836, filed Nov. 21, 2016; 24 pages.
Susanto et al.; "Characteristics, performance and stability of polyethersulfone ultrafiltration membranes prepared by phase separation method using different macromolecular additives"; J. Membr. Sci., vol. 327; 2009; p. 125-35.
U.S. Appl. No. 15/356,836 to Berzinis; Filed with the USPTO on Nov. 21, 2016; 29 pages.
U.S. Appl. No. 62/155,593 to Berzinis; Filed with the USPTO on May 1, 2015; 36 pages.
Written Opinion of the International Search Report for International Application No. PCT/US2016/028951; International Filing Date Apr. 22, 2016; dated Jul. 29, 2016; 9 pages.
Written Opinion of the International Searching Authority for International Application No. PCT/US2017/022061; Date of Filing: Mar. 13, 2017; dated Jul. 4, 2017; 9 pages.
Written Opinion of the International Searching Authority for International Application No. PCT/US2017/022088; Date of Filing: Mar. 13, 2017; dated Jun. 28, 2017; 8 pages.
Advisory Action dated Aug. 8, 2017; U.S. Appl. No: 15/356,836, filed Nov. 21, 2016; 11 pages.
JP 1999322921A; Machine Translation; Date of Publication: Nov. 26, 1999; 30 pages.
International Preliminary Report on Patentability for International Application No. PCT/US2016/028951; Date of Filing: Apr. 22, 2016; dated Aug. 7, 2017; 57 pages.
Written Opnion of the International Searching Authority for International Application No. PCT/US2016/028951; Date of Filing: Apr. 22, 2016; dated Apr. 11, 2017; 10 pages.

\* cited by examiner 14.0% PPE
3.6% P123
82.4% NMP 14.0% PPE
10.0% P123
76.0% NMP

POROUS MEMBRANES AND ASSOCIATED SEPARATION MODULES AND METHODS

CROSS-REFERENCE TO RELATED APPLICATIONS

This application claims priority to U.S. Provisional Application No. 62/314,448, filed on Mar. 29, 2016, the entire contents of which are hereby incorporated by reference.

BACKGROUND

The preparation of porous membranes from resins such as polyarylsulfones (PSU) or polyarylethersulfones (PES) for applications in ultrafiltration is based on the Loeb-Sourirajan process where a polymer solution in N-methyl-2-pyrrolidone (NMP) is cast into a flat sheet or spun into a hollow fiber geometry and coagulated in water. The current processes for preparation of ultrafiltration membranes, especially those for demanding applications such as hemodialysis, also rely on incorporation of polymeric solution modifiers such as poly(vinyl pyrrolidone) (PVP) into the casting solution. The PVP is added at loadings of ~50% by weight of the membrane-forming polymer such as PES, but the majority of the PVP is transferred to the aqueous coagulation bath after coagulation of the PES. The PVP that is solubilized in the NMP/water coagulant stream must be separated and then discarded as a material loss. The presence of PVP also complicates separation and recycle of the NMP from the waste coagulant stream since it tends to decompose under the conditions required to distill the NMP. The PVP often remains in the surface pores of the coagulated membrane and post-treatment with aqueous baths containing sodium hypochlorite (NaOCl) is commonly required to remove unwanted excess PVP from the membrane.

The loss of PVP and added process steps significantly increase the cost and complexity of the processes used to prepare ultrafiltration membranes. Thus there is a need to identify a new material for use in ultrafiltration membranes which will form a nanoporous structure when cast from polar aprotic solvents such as NMP, which forms a self-wetting hydrophilic surface, and which does not leach substantial amounts of polymeric additives into the aqueous coagulant system.

BRIEF DESCRIPTION

A separation module comprises a porous membrane comprising, consisting essentially of, or consisting of a poly (phenylene ether) copolymer comprising 10 to 40 mole percent repeat units derived from 2-methyl-6-phenylphenol and 60 to 90 mole percent repeat units derived from 2,6-dimethylphenol; and a block copolymer comprising backbone or pendant blocks of poly($C_{2-4}$ alkylene oxide). The separation module can be used in devices for wastewater treatment, water purification, desalination, separating water-insoluble oil from oil-containing wastewater, membrane distillation, sugar purification, protein concentration, enzyme recovery, dialysis, liver dialysis, or blood oxygenation.

A system for remote access and control of a dialysis device comprising the separation module comprises a server; the dialysis device, configured to connect to the server through a network; and a client device also configured to connect to the server through the network, wherein the server is configured for: maintaining an access control list to determine whether the client device is authorized to connect to the device; and providing a connection for transfer of data between the dialysis device and the client device.

BRIEF DESCRIPTION OF THE DRAWINGS

Referring now to the drawings.

Figure 1:
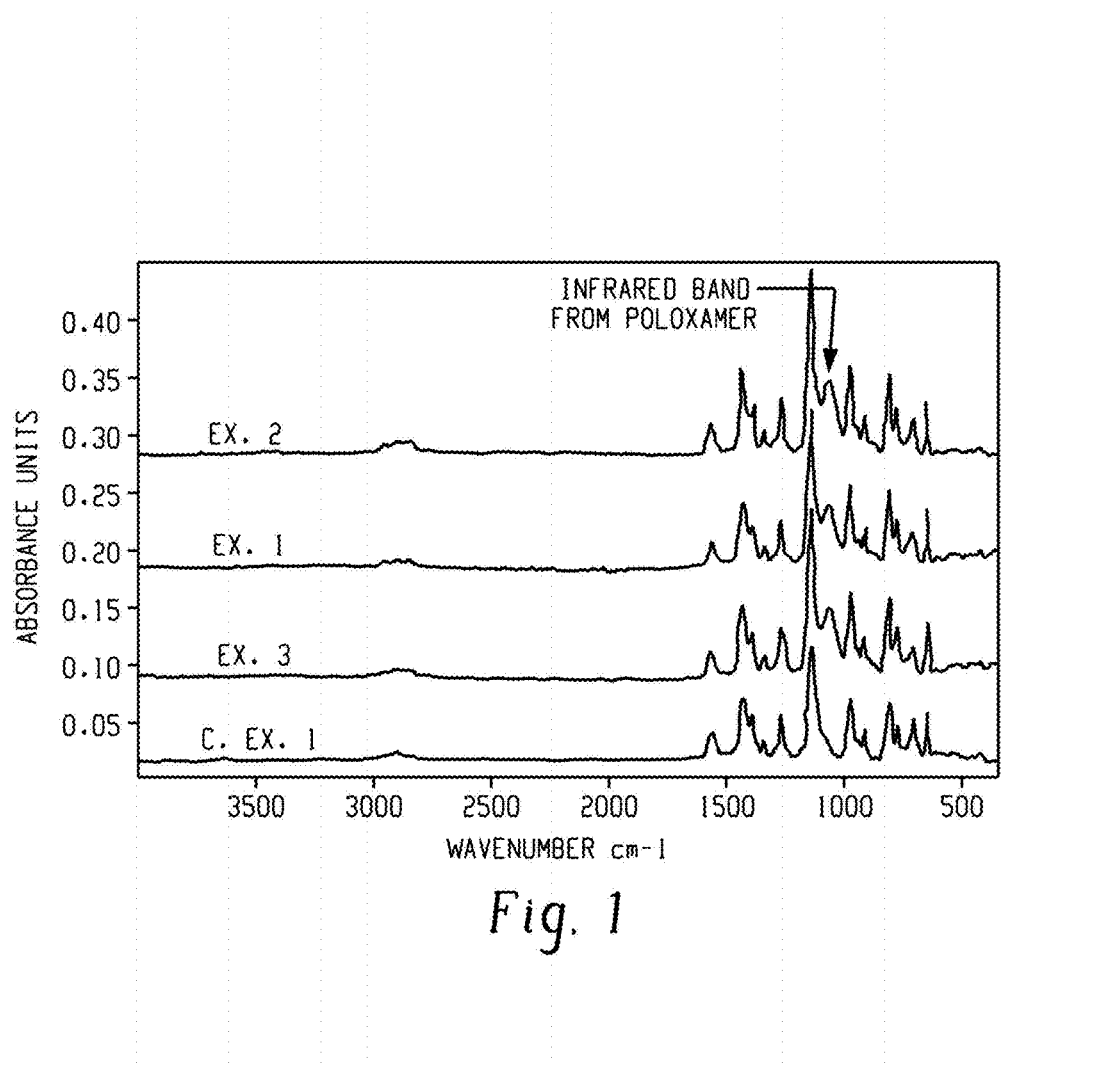
FIG. 1 depicts Fourier Transform Infrared (FTIR) Attenuated Total Reflectance (ATR) spectra of dense membranes of Examples 4-6, composed of 20/80 MPP-DMP copolymer and poloxamers cast from $CHCl_3$.

DETAILED DESCRIPTION inventors hereof have discovered specific hydrophilic block copolymers that are particularly effective in combination with hydrophobic polymers comprising poly(phenylene ether) or poly(phenylene ether) copolymer for the manufacture of porous membranes, including hollow fibers, for use in ultrafiltration. Advantageously, use of the block copolymer in combination with a hydrophobic polymer comprising a poly(phenylene ether) or poly(phenylene ether) copolymer provides porous membranes having surface pore size distributions, surface pore densities, and water contact angles that make them suitable for use in separation modules for purification of aqueous streams by ultrafiltration. The block copolymer provides a hydrophilic surface to porous membranes fabricated from hydrophobic polymers comprising a poly(phenylene ether) or poly(phenylene ether) copolymer, and yet has an affinity for the poly (phenylene ether) or poly(phenylene ether) copolymer, so that the block copolymer is not extracted by washing during fabrication or in end-use operation of the porous membrane during ultrafiltration. Advantageously, the use of the block copolymer in combination with poly(phenylene ether) or poly(phenylene ether) copolymer provides ultrafiltration membranes having a nanoporous structure when cast from polar aprotic solvents such as N-methyl-2-pyrrolidone, and provides a self-wetting hydrophilic surface for the porous membrane. Moreover, the block copolymer is not leached into the aqueous coagulant or aqueous washes during fabrication, or into aqueous streams during ultrafiltration. The porous membranes in various configurations find wide application in separation modules for a variety of ultrafiltration methods.

A separation module comprises a porous membrane comprising, consisting essentially of, or consisting of a poly (phenylene ether) copolymer comprising 10 to 40 mole percent repeat units derived from 2-methyl-6-phenylphenol and 60 to 90 mole percent repeat units derived from 2,6-dimethylphenol; and a block copolymer comprising backbone or pendant blocks of poly($C_{2-4}$ alkylene oxide).

The poly(phenylene ether) copolymer comprises a poly (2-methyl-6-phenyl-1,4-phenylene ether-co-2,6-dimethyl-1,4-phenylene) copolymer having 10 to 40 mole percent of repeat units derived from 2-methyl-6-phenylphenol and 60 to 90 mole percent repeat units derived from 2,6-dimethylphenol. Within this range, the poly(phenylene ether) copolymer can comprise greater than or equal to 12.5, 15, or 20 mole percent and less than or equal to 35, 30, or 25 mole percent 2-methyl-6-phenylphenol, and greater than or equal to 35, 40, or 45 mole percent and less than or equal to 80 or 85 mole percent 2,6-dimethylphenol. The inventors have discovered the criticality of the amount of 2-methyl-6-phenylphenol (MPP) comonomer. Below about 10 mole percent 2-methyl-6-phenylphenol, the copolymer does not have sufficient solubility in the dope solution used to prepare the porous membrane. Above about 40 mole percent 2-methyl-6-phenylphenol, it can be difficult to incorporate that much 2-methyl-6-phenylphenol into the copolymer due to its lower reactivity relative to 2,6-dimethylphenol; the viscosity of the dope solution at suitable copolymer concentrations can be too low to produce porous membranes; and the copolymer can be too costly. In the range of about 10 to 40 mole percent 2-methyl-6-phenylphenol, solubility, viscosity, and cost of the copolymer, and incorporation of the 2-methyl-6-phenylphenol is optimized.

The hydrophobic polymer can be a poly(phenylene ether) copolymer having an intrinsic viscosity of 0.6 to 1.5 deciliters per gram, measured in chloroform at 25° C. using an Ubbelohde viscometer. Within this range, the intrinsic viscosity can be greater than or equal to 0.7, 0.8, 0.9, 1.0, or 1.1 deciliters per gram, and less than or equal to 1.4, or 1.3 deciliters per gram. In some embodiments, the intrinsic viscosity is 0.7 to 1.1 deciliters per gram, or 0.7 to 0.9 deciliters per gram. In some embodiments, The poly(phenylene ether) copolymer can also have a weight average molecular weight of 75,000 to 500,000 daltons (Da), as measured by gel permeation chromatography against polystyrene standards. Within this range, the weight average molecular weight can be greater than or equal to 100,000 or 200,000 Da and less than or equal to 400,000, 350,000, or 300,000 Da. In some embodiments, the weight average molecular weight is 75,000 to 200,000 Da, specifically 100,000 to 150,000 Da. The poly(phenylene ether) copolymer can have a polydispersity (ratio of weight average molecular weight to number average molecular weight of 2 to 12. Within this range, the polydispersity can be greater than or equal to 3 or 4 and less than or equal to 10, 9, or 8. In some embodiments, the poly(phenylene ether) copolymer has an intrinsic viscosity of 0.6 to 1.5 deciliters per gram, measured in chloroform at 25° C. and a weight average molecular weight of 75,000 to 500,000 daltons, measured by gel permeation chromatography against polystyrene standards.

The solubility of the poly(phenylene ether) copolymer in a water-miscible polar aprotic solvent can be greater than or equal to 50 grams per kilogram at 25° C., based on the combined weight of the hydrophobic polymer and the solvent. Within this range, the solubility can be greater than or equal to 100, 120, 140, or 160 grams per kilogram, and less than or equal to 400, 300, 250, 200, or 180 grams per kilogram at 25° C. The polar aprotic solvent can be, for example N-methyl-2-pyrollidone, N,N-dimethylformamide, or N,N-dimethylacetamide. Advantageously, the use poly (phenylene ether) copolymers having an intrinsic viscosity of 0.6 to 1.5 deciliters per gram, specifically 0.7 to 1.1 deciliters per gram or 0.7 to 0.9 deciliters per gram, and a solubility of 50 to 400 grams per kilogram at 25° C. results in membrane-forming compositions with solution concentrations and viscosities that provide good control over the phase inversion step of membrane formation.

The porous membrane comprises a block copolymer comprising backbone or pendant blocks of poly($C_{2-4}$ alkylene oxide). The poly($C_{2-4}$ alkylene oxide) is derived from polymerization of ethylene oxide, propylene oxide, 1,2-butylene oxide, or a combination comprising at least one of the foregoing. In some embodiments, the block copolymer is a poly(ethylene oxide)-poly(propylene oxide)-poly(ethylene oxide) block copolymer, a poly(ethylene oxide)-poly(propylene oxide)-poly(ethylene oxide) block copolymer, a poly ($C_{2-4}$ alkylene oxide)-poly(dimethylsiloxane) block copolymer, or a combination comprising at least one of the foregoing.

In some embodiments, the porous membrane comprises 20 to 90 weight percent poly(phenylene ether) copolymer and 10 to 80 weight percent block copolymer, based on the total weight of the porous membrane. Within this range, the porous membrane can comprise greater than or equal to 30, 40, 50 or 60 weight percent and less than or equal to 80 or 70 weight percent, poly(phenylene ether) copolymer, and greater than or equal to 20, 30, 40, 50 or 60 weight percent and less than or equal 70 weight percent, of the block copolymer. In some embodiments, the porous membrane comprises 60 to 90 weight percent poly(phenylene ether) copolymer and 10 to 40 weight percent block copolymer; or 60 to 80 weight percent poly(phenylene ether) copolymer, and 20 to 40 weight percent block copolymer. The inventors have discovered that the amount of block copolymer in the porous membrane can affect the porous membrane properties. For example, when the poly(phenylene ether) copolymer is derived from 20 mole percent 2-methyl-6-phenylphenol and 80 mole percent 2,6-dimethylphenol, and the block copolymer is poly(ethylene oxide)-poly(propylene oxide)-poly(ethylene oxide) having 30 weight percent polypropylene oxide blocks and a number average molecular weight of 5,000 Da, greater than about 40 weight percent of the block copolymer is required to obtain a self-wetting porous membrane.

In some embodiments, the block copolymer comprises a poloxamer. A poloxamer is a poly(ethylene oxide)-poly (propylene oxide)-poly(ethylene oxide) block copolymer or a poly(propylene oxide)-poly(ethylene oxide)-poly(propylene oxide) block copolymer. In some embodiments, the block copolymer comprises a poly(ethylene oxide)-poly(propylene oxide)-poly(ethylene oxide) block copolymer having a number average molecular weight of 1,000 to 14,000 daltons. Within this range, the block copolymer can have a number average molecular weight greater than or equal to 2,000 daltons and less than or equal to 12,000, 10,000, 8,000, 6,000, or 4,000 daltons, specifically 2,000 to 6,000 daltons. The poly(ethylene oxide)-poly(propylene oxide)-poly(ethylene oxide) block copolymer can also comprise, based on the weight of the block copolymer, 1 to 90 weight percent poly(ethylene oxide) blocks. Within this range, the block copolymer can comprise greater than or equal to 5 weight percent and less than or equal to 80, 50, 40, or 30 weight percent, specifically 5 to 50 weight percent, of poly(ethylene oxide) blocks.

In some embodiments, the block copolymer comprises a poly(propylene oxide)-poly(ethylene oxide)-poly(propylene oxide) block copolymer having a number average molecular weight of 500 to 12,000 daltons. Within this range, the block copolymer can have a number average molecular weight of greater than or equal to 1,000, or 2,000 daltons and less than or equal to 10,000, 8,000, or 6,000 daltons, specifically 2,000 to 10,000 daltons. The poly(propylene oxide)-poly(ethylene oxide)-poly(propylene oxide) block copolymer can also comprise, based on the weight of the block copolymer, 1 to 90 weight percent of poly(ethylene oxide) blocks. Within this range, the block copolymer can comprise greater than or equal to 5 weight percent and less than or equal to 80, 50, 40, or 30 weight percent, specifically 5 to 50 weight percent, of poly(ethylene oxide) blocks. In some embodiments, the block copolymer comprises a combination of the poly(propylene oxide)-poly(ethylene oxide)-poly(propylene oxide) block copolymer and poly(propylene oxide)-poly(ethylene oxide)-poly(propylene oxide) block copolymer described herein.

Poloxamers are available from BASF under the PLURONIC™ trade name and from Croda under the SYNPERONIC™ trade name. Some commercial examples are listed in Table 1 below.

TABLE 1

Commercially Available Poloxamers

| Trade Name | $M_n$ (Da) | Structure | PEO Content (wt. %) |
|---|---|---|---|
| PLURONIC ™ 31R1 | 3,300 | (II) x + z = 52, y = 8; x = z = 26[a] | 10 |
| PLURONIC ™ L81 | 2,800 | (I) x + z = 6, y = 44; x = z = 3[a] | 10 |
| PLURONIC ™ P123 | 5,800 | (I) x + z = 40, y = 70; x = z = 20[a] | 30 |
| SYNPERONIC ™ L62 | 2,250 | (I) | 20 |
| SYNPERONIC ™ L64 | 3,000 | (I) | 40 |
| SYNPERONIC ™ L101 | 3,300 | (I) | 10 |
| PLURONIC ™ 17R2 | 2,200 | (II) | 20 |
| PLURONIC ™ 17R4 | 2,800 | (II) | 40 |

[a]Most prevalent polymer.

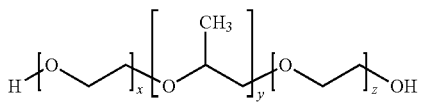

(I)

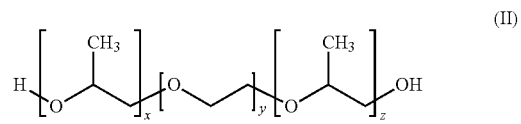

(II)

In some embodiments, the block copolymer comprises a poly($C_{2-4}$ alkylene oxide)-polysiloxane block copolymer comprising, based on the total weight of the block copolymer, 5 to 60 weight percent polysiloxane. Within this range, the poly($C_{2-4}$ alkylene oxide)-polysiloxane block copolymer can comprise greater than or equal to 10, 15, or 20 weight percent and less than or equal to 50 or 40 weight percent, specifically 20 to 40 weight percent, polysiloxane. The poly($C_{2-4}$ alkylene oxide)-polysiloxane block copolymer can also have a number average molecular weight of 500 to 14,000 daltons. Within this range, the number average molecular weight can be greater than or equal to 1000 or 2000 daltons and less than or equal to 12,000, 10,000, 8,000 or 6,000 daltons, specifically 1,000 to 6,000 daltons.

The poly($C_{2-4}$ alkylene oxide)-polysiloxane block copolymer can have the structure:

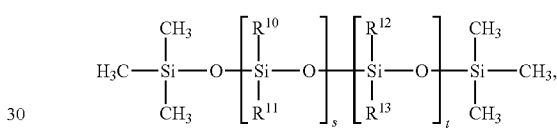

wherein $R^{10}$, $R^{11}$, $R^{12}$, and $R^{13}$ are each independently a $C_1$-$C_{12}$ alkyl, aryl, alkaryl, aralkyl, alkoxy, substituted alkyl, substituted aryl, or Q, provided that at least one of $R^{11}$, $R^{12}$, and $R^{13}$ is Q, and s and t are each independently an integer from 1 to 50; and wherein Q has the structure:

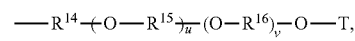

wherein $R^{14}$ is a $C_1$-$C_{10}$ alkylene; $R^{15}$ and $R^{16}$ are each independently $C_{2-4}$ alkylene; T is hydrogen, methyl, butyl, or acetyl; and u and v are each independently integers from 1 to 20.

In some embodiments, the block copolymer comprises a poly($C_{2-4}$ alkylene oxide)-poly(dimethylsiloxane) block copolymer of structure:

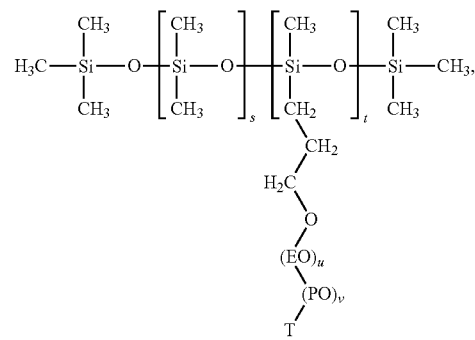

wherein: EO is —$CH_2$—$CH_2$—O—; PO is —$CH_2$—CH($CH_3$)—O—; T is hydrogen, methyl, butyl, or acetyl; s and t are each independently an integer from 1 to 50; u is an integer from 1 to 20; and v is an integer from 0 to 20.

The porous membrane can have a uniform distribution of pores throughout its thickness, i.e. it can have a uniform density along a cross-section. The porous membrane can also have a non-uniform distribution of pores throughout its thickness, i.e. it can have a non-uniform density along its thickness. For example, the membrane can be a porous asymmetric membrane, i.e. it can have a gradation of pore size from large to small along a cross-section.

The porous membrane comprising a poly(phenylene ether) or poly(phenylene ether) copolymer, and a block copolymer comprising backbone or pendant blocks of poly(alkylene oxide), exhibits many advantageous surface properties. The block copolymer comprising backbone or pendant poly(alkylene oxide) is incorporated into the selective surface layer of the porous membrane by the method, which advantageously reduces the water contact angle of the surface compared to a porous membrane made from the hydrophobic polymer without the block copolymer. The lower the water contact angle of the porous membrane, the more likely the membrane will be self-wetting. For example, the porous membrane can have a water contact angle of greater than or equal to 20, 30, or 40 degrees, and less than or equal to 80, 70, or 60 degrees. In some embodiments, the porous membrane has a water contact angle of 20 to 80 degrees. The porous membrane made by the method can have a mean surface pore size distribution on the selective layer of greater than or equal to 1, 5, 10 nanometers (nm) and less than or equal to 100, 50, or 20 nm±1, 2, 5, or 10 nm. The porous membrane made by the method can also have a surface pore density of greater than or equal to 100, 200, or 400 pores per $\mu m^2$ and less than or equal to 4,000, 2,400, or 1,200 pores per $\mu m^2$.

A method of forming the porous membrane, comprises: dissolving a poly(phenylene ether) copolymer comprising 10 to 40 mole percent repeat units derived from 2-methyl-6-phenylphenol and 60 to 90 mole percent repeat units derived from 2,6-dimethylphenol and, a block copolymer comprising backbone or pendant blocks of poly($C_{2-4}$ alkylene oxide) in a water-miscible polar aprotic solvent to form a porous membrane-forming composition; and phase-inverting the porous membrane forming-composition in a first non-solvent composition to form the membrane. All of the properties of the porous membrane disclosed herein apply as well to the method of making the porous membrane. For example, the method of forming the porous membrane can comprise: dissolving a hydrophobic polymer comprising, consisting essentially of, or consisting of a poly(phenylene ether) copolymer comprising 50 to 90 mole percent repeat units derived from 2,6-dimethylphenol; and 10 to 50 mole percent repeat units derived from 2-methyl-6-phenylphenol; and a block copolymer, wherein the block copolymer is a poly(ethylene oxide)-poly(propylene oxide)-poly(ethylene oxide) block copolymer, a poly(ethylene oxide)-poly(propylene oxide)-poly(ethylene oxide) block copolymer, a poly($C_{2-4}$ alkylene oxide)-poly(dimethylsiloxane) block copolymer, or a combination comprising at least one of the foregoing, in N-methyl-2-pyrrolidone to form a porous membrane-forming composition; and phase-inverting the porous membrane forming-composition in a first non-solvent composition comprising water, N-methyl-2-pyrrolidone, or a combination comprising at least one of the foregoing, to form the porous membrane.

In some embodiments, the membrane-forming composition comprises, based on the total weight of the composition, 1 to 50 weight percent, specifically 10 to 40 weight percent, of the hydrophobic polymer and block copolymer comprising backbone or pendant blocks of poly($C_{2-4}$ alkylene oxide) combined, and 50 to 99 weight percent, specifically 60 to 90 weight percent, of the water-miscible polar aprotic solvent, and has a viscosity of 1 to 100 pascal·seconds, specifically 1 to 20 pascal·seconds. In some embodiments of the method, the block copolymer comprising backbone or pendant blocks of poly($C_{2-4}$ alkylene oxide) is dissolved in the first non-solvent composition instead of the membrane-forming composition.

The poly(phenylene ether) copolymer is dissolved in a water-miscible polar aprotic solvent to form the membrane-forming composition. The water-miscible polar aprotic solvent can be, for example, N,N-dimethylformamide (DMF), N,N-dimethylacetamide (DMAC), N-methyl-2-pyrollidone (NMP), N-ethyl-2-pyrrolidone, dimethyl sulfoxide (DMSO), dimethyl sulfone, sulfolane, butyrolactone; and combinations comprising at least one of the foregoing. In some embodiments, the water-miscible polar aprotic solvent is N-methyl-2-pyrollidone. The solubility of the poly(phenylene ether) copolymer in the water-miscible polar aprotic solvent can be greater than 50 grams per kilogram at 25° C., based on the combined weight of the poly(phenylene ether) and the solvent. Within this range, the solubility can be greater than or equal to 100, 120, 140, or 160 grams per kilogram, and less than or equal to 400, 300, 250, 200, or 180 grams per kilogram at 25° C. Solubility can be determined in N-methyl-2-pyrrolidone, N,N-dimethylformamide, or N,N-dimethylacetamide. Advantageously, a poly(phenylene ether) copolymer solubility of 50 to 400 grams per kilogram provides membrane-forming compositions conducive to the formation of suitable porous membranes. The membrane-forming composition can also comprise a polar protic co-solvent, for example glycerin, isopropanol, or water, to modify viscosity and cloud point of the membrane-forming composition, and thereby modify the pore structures of porous membranes made from the membrane-forming compositions.

The first non-solvent composition comprises water, a water-miscible polar aprotic solvent, or a combination comprising at least one of the foregoing. The water-miscible polar aprotic solvent can be any of the water-miscible polar aprotic solvents used for the membrane-forming composition. In some embodiments, the first non-solvent composition comprises, based on the total weight of the first non-solvent composition, 10 to 100 weight percent water and 0 to 90 weight percent N-methyl-2-pyrrolidone, based on the total weight of the first non-solvent composition. Within this range, the first non-solvent composition can comprise 10 to 90 weight percent, specifically 10 to 80 weight percent, water and 10 to 90 weight percent, specifically 20 to 90 weight percent, N-methyl-2-pyrrolidone. In some embodiments, the first non-solvent composition comprises about 75 weight percent water and about 25 weight percent N-methyl-2-pyrrolidone. The first non-solvent composition serves as a coagulation, or phase inversion, bath for the membrane-forming composition. The porous membrane is formed by contacting the membrane-forming composition with the first non-solvent composition. The hydrophobic polymer, which is near its gel point in the membrane-forming composition, coagulates, or precipitates as a porous film or hollow fiber, depending on the method used. As mentioned above, in some embodiments of the method, the block copolymer comprising backbone or pendant blocks of poly(alkylene oxide) is dissolved in the first non-solvent composition instead of the membrane-forming composition.

The method includes phase-inverting the membrane-forming composition in the first non-solvent composition. Any of several techniques for phase inversion can be used. For example, the phase inversion can be a dry-phase separation method in which the dissolved copolymer is precipitated by evaporation of a sufficient amount of solvent mixture to form the membrane. The phase inversion step can also be a wet-phase separation method in which the dissolved copolymer is precipitated by immersion in the first non-solvent to form the membrane. The phase inversion step can be a dry-wet phase separation method, which is a combination of the dry-phase and the wet-phase methods. The phase inversion step can be a thermally-induced separation method in which the dissolved copolymer is precipitated or coagulated by controlled cooling to form the membrane. The porous membrane, once formed, can be subjected to membrane conditioning or pretreatment, prior to its end-use. The conditioning or pretreatment can be thermal annealing to relieve stresses, and/or wetting and pre-equilibration of the porous membrane in the expected feed stream.

In some embodiments, the method further comprises washing the porous membrane in a second non-solvent composition. This washing step can be repeated one or more times. The number of washing steps should be sufficient to rinse any residual block copolymer comprising backbone or pendant blocks of poly($C_{2-4}$ alkylene oxide) not adhered to the porous membrane, and any residual water-miscible polar aprotic solvent, from the porous membrane. The first and second non-solvent compositions can be the same or different, and can comprise water or a mixture of water and a water-miscible polar aprotic solvent. In some embodiments, the first and second non-solvent compositions are water or a mixture of water and N-methyl-2-pyrrolidone. In some embodiments, the first and second non-solvent compositions are both water. The water can be deionized. In some embodiments, the method further comprises drying the porous membrane to remove residual first and second non-solvent composition, for example water and N-methyl-2-pyrrolidone.

The method is also applicable to making hollow fibers by coextrusion of a dope solution and a bore fluid, in which the membrane-forming composition is the dope solution and the first non-solvent composition is the bore fluid. Thus in some embodiments, a method of making a hollow fiber by coextrusion through a spinneret comprising an annulus and a bore, comprises coextruding a membrane-forming composition comprising a poly(phenylene ether) copolymer comprising 10 to 40 mole percent repeat units derived from 2-methyl-6-phenylphenol and 60 to 90 mole percent repeat units derived from 2,6-dimethylphenol, and a block copolymer comprising backbone or pendant blocks of poly($C_{2-4}$ alkylene oxide) dissolved in a water-miscible polar aprotic solvent through the annulus, and a first non-solvent composition comprising water, a water-miscible polar aprotic solvent, or a combination comprising at least one of the foregoing, through the bore, into a second non-solvent composition comprising water, a water-miscible polar aprotic solvent, or a combination comprising at least one of the foregoing, to form the hollow fiber. In some embodiments of the method, the block copolymer comprising backbone or pendant blocks of poly(alkylene oxide) is dissolved in the first non-solvent composition (bore fluid) instead of the membrane-forming composition (dope solution).

In some embodiments the method further comprises washing the hollow fiber in a third non-solvent composition. This washing step can be repeated one or more times. These steps serve to rinse any residual water-miscible polar aprotic solvent from the hollow fibers. The second and third non-solvent compositions can be the same or different, and can comprise water or a mixture of water and a water-miscible polar aprotic solvent. In some embodiments the second and third non-solvent compositions are independently water or a mixture of water and N-methyl-2-pyrrolidone. In some embodiments, the second and third non-solvent compositions are each water. The water can be deionized. In some embodiments, the method further comprises drying the hollow fiber to remove residual second and third non-solvent composition, for example water and N-methyl-2-pyrrolidone.

A hollow fiber used in the separation module is made by coextruding through a spinneret comprising an annulus and a bore: a membrane-forming composition comprising a poly(phenylene ether) copolymer and a block copolymer comprising backbone or pendant blocks of poly($C_{2-4}$ alkylene oxide) dissolved in a water-miscible polar aprotic solvent through the annulus, and a first non-solvent composition comprising water, a water-miscible polar aprotic solvent, or a combination comprising at least one of the foregoing, through the bore, into a second non-solvent composition comprising water, a water-miscible polar aprotic solvent, or a combination comprising at least one of the foregoing, to form the hollow fiber.

The hollow fibers can be used in various separation modules. Thus in some embodiments, a separation module comprises hollow fiber made by coextruding through a spinneret comprising an annulus and a bore: a membrane-forming composition comprising a poly(phenylene ether) copolymer comprising 10 to 40 mole percent repeat units derived from 2-methyl-6-phenylphenol and 60 to 90 mole percent repeat units derived from 2,6-dimethylphenol block copolymer comprising backbone or pendant blocks of poly($C_{2-4}$ alkylene oxide) through the annulus, and a first non-solvent composition comprising water, a water-miscible polar aprotic solvent, or a combination comprising at least one of the foregoing, and a polymer additive dissolved in the first non-solvent composition, through the bore, into a second non-solvent composition comprising water, a water-miscible polar aprotic solvent, or a combination comprising at least one of the foregoing, to form the hollow fiber.

The porous membranes can be fabricated into separation modules designed for purification of various aqueous, non-aqueous (e.g., hydrocarbon), or gaseous streams. Thus in some embodiments, a separation module comprises the porous membrane comprising a poly(phenylene ether) copolymer; and a block copolymer comprising 10 to 40 mole percent repeat units derived from 2-methyl-6-phenylphenol and 60 to 90 mole percent repeat units derived from 2,6-dimethylphenol and a block copolymer comprising backbone or pendant blocks of poly($C_{2-4}$ alkylene oxide).

The separation module can comprise the porous membrane in a sheet, disc, spiral wound, plate and frame, hollow fiber, capillary, or tubular configuration. The separation module can be designed for dead-end separation, cross-flow separation, inside-out separation, or outside-in separation. Outside-in and inside-out separations are applicable to hollow fiber membranes, capillary membranes, and tubular membranes, each having an inner and outer surface in contact with the feed and retentate or the permeate. In some embodiments of the separation module, the porous membrane is a flat sheet. In some embodiments of the separation module, the porous membrane is a flat sheet in a spiral-wound configuration. In some embodiments of the separation module, the porous membrane is a flat sheet is in a plate and frame configuration. In some embodiments of the separation module, the porous membrane is in a capillary or tubular configuration.

The porous membrane made by the method can be a hollow fiber. The wall thickness of the hollow fiber can be 10 to 200 micrometers. Within this range, the diameter can greater than 20 and less than or equal to 80, 60, 40, or 35 micrometers. In another embodiment the diameter can be 50 to 5000 micrometers (μm), specifically 100 to 2000 μm. The membrane can comprise a substantially non-porous surface layer, and the non-porous surface layer can be on the inside surface of the hollow fiber. A separation module can comprise bundles of porous hollow fibers. In some embodiments, the fiber bundle comprises 10 to 10,000 porous hollow fibers. The hollow fibers can be bundled longitudinally, potted in a curable resin on both ends, and encased in a pressure vessel to form the hollow fiber module. Hollow fiber modules can be mounted vertically or horizontally.

In some embodiments, the separation module comprises: an enclosure configured to contain a bundle of the hollow fibers, the enclosure having an outlet configured for withdrawing a permeate fluid; a first encasement comprising a thermoset or a thermoplastic polymeric material and located at a first end of the bundle, arranged such that the hollow fiber membranes are embedded in the first encasement and communicate through the first encasement and are open on an outer face of the first encasement; a second encasement comprising a thermoset or a thermoplastic polymeric material and located at a second end of the bundle opposite the first end of the bundle, arranged such that the hollow fiber membranes are embedded in the second encasement and communicate through the second encasement and are open on an outer face of the second encasement; a first end cap arranged and configured for attaching and sealing to the first end of the bundle or enclosures at or near the first encasement; a second end cap arranged and configured for attaching and sealing to the second end of the bundle or enclosures at or near the second encasement; an inlet for introducing a fluid mixture to be separated into bores of the hollow fiber membranes at the first encasement; and an outlet for withdrawing a retentate fluid from the bores for the hollow fiber membranes at the second encasement.

Depending upon porous membrane surface pore size distribution and pore density, and the end-use, the separation module fabricated from the porous membrane made by the method can be a media filtration module, a microfiltration module, an ultrafiltration module, a nanofiltration module, or a reverse osmosis module. The separation module fabricated from the porous membrane made by the method can also be a membrane contactors module, a pervaporation module, a dialysis module, an osmosis module, an electrodialysis module, a membrane electrolysis module, an electrophoresis module, or a membrane distillation module. For media filtration, the surface pore size can be about 100 to about 1,000 micrometers (μm). For microfiltration, the surface pore size can be about 0.03 to about 10 micrometers. For ultrafiltration, the surface pore size can be about 0.002 to 0.1 micrometers. For nanofiltration, the surface pore size can be about 0.001 to about 0.002 micrometers. The porous membranes described herein are surprisingly well suited for ultrafiltration and nanofiltration. In some embodiments, the porous membrane has a surface pore size of 0.001 to 0.05 micrometers, specifically 0.005 to 0.01 micrometers.

The molecular weight cut off (MWCO) of a membrane is the lowest molecular weight solute in which 90 weight percent (wt %) or greater of the solute is retained by the membrane. The porous membranes made by the method can have a MWCO of 500 to 100,000 daltons (Da), specifically 1,000 to 50,000 Da, more specifically 2,000 to 35,000 Da, or still more specifically 3,000 to 10,000 Da. Furthermore, any of the foregoing MWCO ranges can be present in combination with a desirable permeate flux, such as clean water permeate flux (CWF). For example, the permeate flux can be 1 to 1,000 L/(h·m$^2$·bar), specifically 2 to 200 L/(h·m$^2$·bar), and more specifically 4 to 50 L/(h·m$^2$·bar), wherein L is liters and m$^2$ is square meters. The porous membranes made by the method can also provide a CWF of about 10 to about 80 L/(h·m$^2$·bar), about 20 to about 80 L/(h·m$^2$·bar), or about 40 to about 60 L/(h·m$^2$·bar). Flux across the membrane is driven by the osmotic or absolute pressure differential across the membrane, referred to herein as the trans-membrane pressure (TMP). The trans-membrane pressure can be 1 to 2,500 kilopascals (kPa), specifically 2 to 400 kPa, and more specifically 4 to 300 kPa.

The porous membranes made by the method are useful for treatment of a variety of aqueous streams. Depending upon surface pore size distribution and pore density, and the configuration of the porous membrane, the porous membrane can be used to remove one or more of the following contaminants from water: suspended matter, particulate matter, sands, silt, clays, cysts, algae, microorganisms, bacteria, viruses, colloidal matter, synthetic and naturally occurring macromolecules, dissolved organic compounds, and salts. Thus, separation modules fabricated from the porous membranes can be used in wastewater treatment, water purification, food processing, and in the dairy, biotechnology, pharmaceutical, and healthcare industries.

Separation modules fabricated from the porous membranes can advantageously be used in biomedical, pharmaceutical, biotechnological, or food processes, for example the removal of salts and/or low molecular weight organic impurities from aqueous fluids by ultrafiltration, which results in increased concentration of a material having a molecular weight above the cut-off of the porous membrane in an aqueous fluid. For example, separation modules fabricated from the porous membrane can be used for the production of purified water, e.g., drinking water; pretreatment of water in desalination systems; removal of contaminants, including biological contaminants such as bacteria or protozoa, or organic chemical contaminants such as polychlorinated biphenyls (PCBs), to produce purified water; wastewater treatment; or membrane distillation. Thus in some embodiments, a device for wastewater treatment, water purification, desalination, or separating water-insoluble oil from oil-containing wastewater, comprises the separation module. In some embodiments, a device for purification of a liquid by membrane distillation comprises the separation module.

Advantageously, separation modules fabricated from the porous membrane can be used for the purification of biochemical materials in various aqueous fluids. The aqueous fluid can be, for example, human blood, animal blood, lymph fluids, microbial or cellular suspensions, for example suspensions of bacteria, alga, plant cells, or viruses. Specific biochemical applications include the concentration and purification of peptides in blood plasma; enzyme recovery, protein recovery, and desalting of proteins. Specific food applications include separation of polysaccharides, wherein separation comprises contacting an aqueous mixture of sugars, such as dextrose, glucose and fructose, with the porous membrane to provide a fluid enriched in a desired sugar; ultrafiltration of meat products and by-products, plant extracts, suspensions of algae or fungi, vegetable food and beverages containing particles such as pulp, and the production of milk protein concentrate for the production of cheese. Other applications include downstream processing of fermentation broths; concentration of protein in whole egg or egg white with simultaneous removal of salts and sugars; and concentration of gelling agents and thickeners, for example agar, carrageenan, pectin, or gelatin. Thus in some embodiments, a device for sugar purification, protein concentration, or enzyme recovery, comprises the separation module.

The aqueous fluid to be purified can also be human blood, animal blood, or lymph fluids. In particular, the separation module comprising a hollow fiber, or a bundle of hollow fibers as described above can be used in biomedical applications, for example hemodialysis, hemofiltration, or hemodiafiltration (a combination of hemofiltration and hemodialysis) for renal failure, liver dialysis for liver failure, or for oxygenation of blood, such as in an artificial lung device. Thus, in some embodiments, a dialysis device for conducting hemodialysis or hemodialysis on a patient suffering from renal failure, comprises a separation module comprising a hollow fiber, or a bundle of hollow fibers as described above. A dialysis device for conducting liver dialysis on a patient suffering from liver failure comprises a separation module comprising a hollow fiber, or a bundle of hollow fibers as described above. A blood oxygenator comprises a separation module comprising a hollow fiber, or a bundle of hollow fibers as described above.

Figure 6:
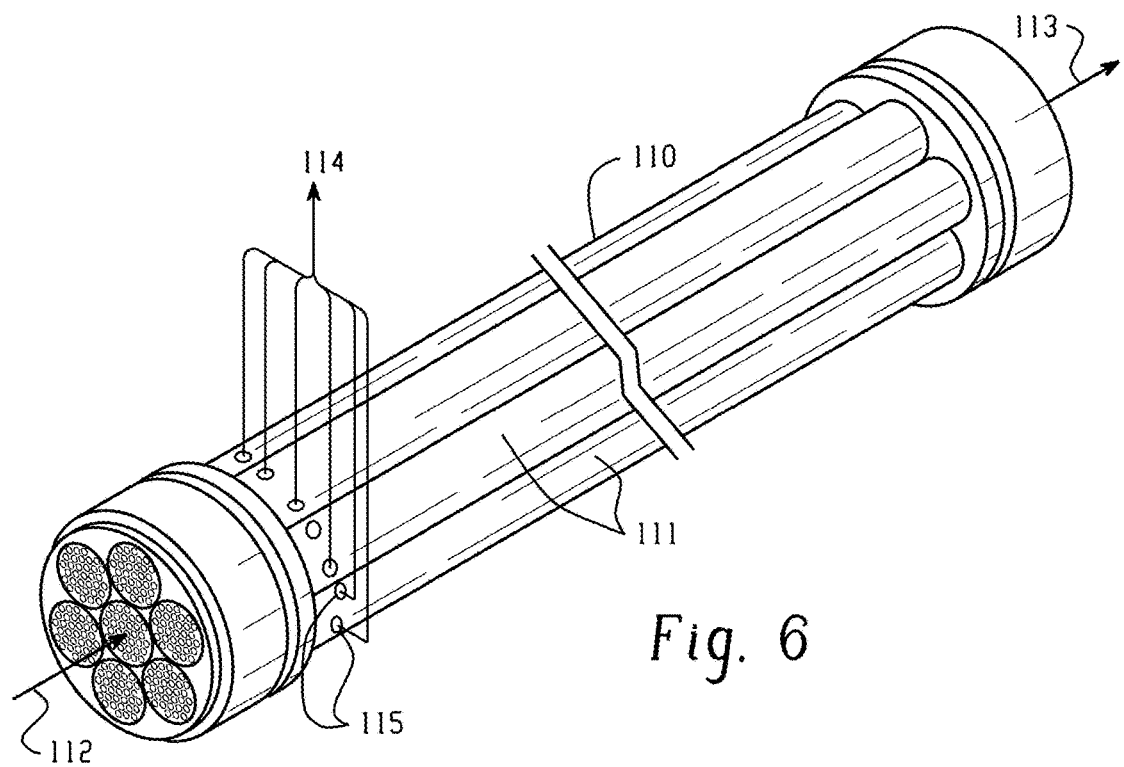
FIG. 6 shows an embodiment of a hollow fiber separation module.

Disclosed in FIG. 6 is an embodiment of a separation module 110 comprising one or more bundles of hollow fibers of the asymmetric membrane. Each fiber bundle may be contained within an enclosure 111 that is substantially impermeable to the fluids to be separated to prevent fluid from passing between adjacent fiber bundles. The hollow fibers may be embedded in and communicate through an encasement 116 at either end of the module. The encasement may comprise a thermoset, such as epoxy, polyester, melamine, polysiloxane, or a polyurethane; or may comprise a thermoplastic, such as polyethylene, polypropylene, poly(ethylene terephthalate), or poly(1,4-butylene terephthalate), for example. The feed stream 112 enters the bore of the fibers at one end of the module and the retentate stream 113 leaves at the opposite end. The encasement may be disposed at ends of the bundles for attaching and sealing to the bundles. The permeate 114 can be recovered from holes 115 disposed in a side of the enclosure, alternatively the permeate may be recovered from holes in the encasement.

Figure 7:
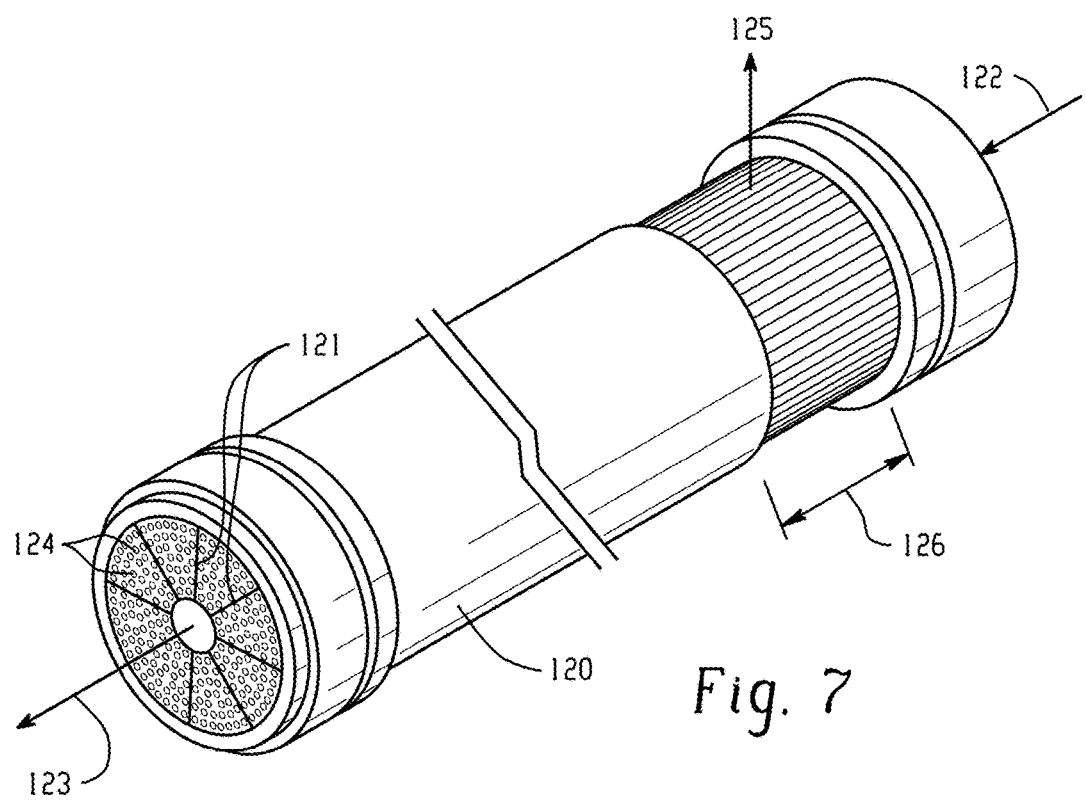
FIG. 7 shows another embodiment of a hollow fiber separation module.

The fiber bundles need not be cylindrical. For example, shown in FIG. 7 is an embodiment of a separation module 120 in which the bundles of fibers are separated by an impermeable barrier 121. In the separation module 120, the feed stream 122 enters the bores of the hollow fibers at one end of the bundles 124 and the retentate stream 123 exits at the opposite end. The permeate fluid 125 can exit the module through an opening 126 in a side of the module.

Figure 8:
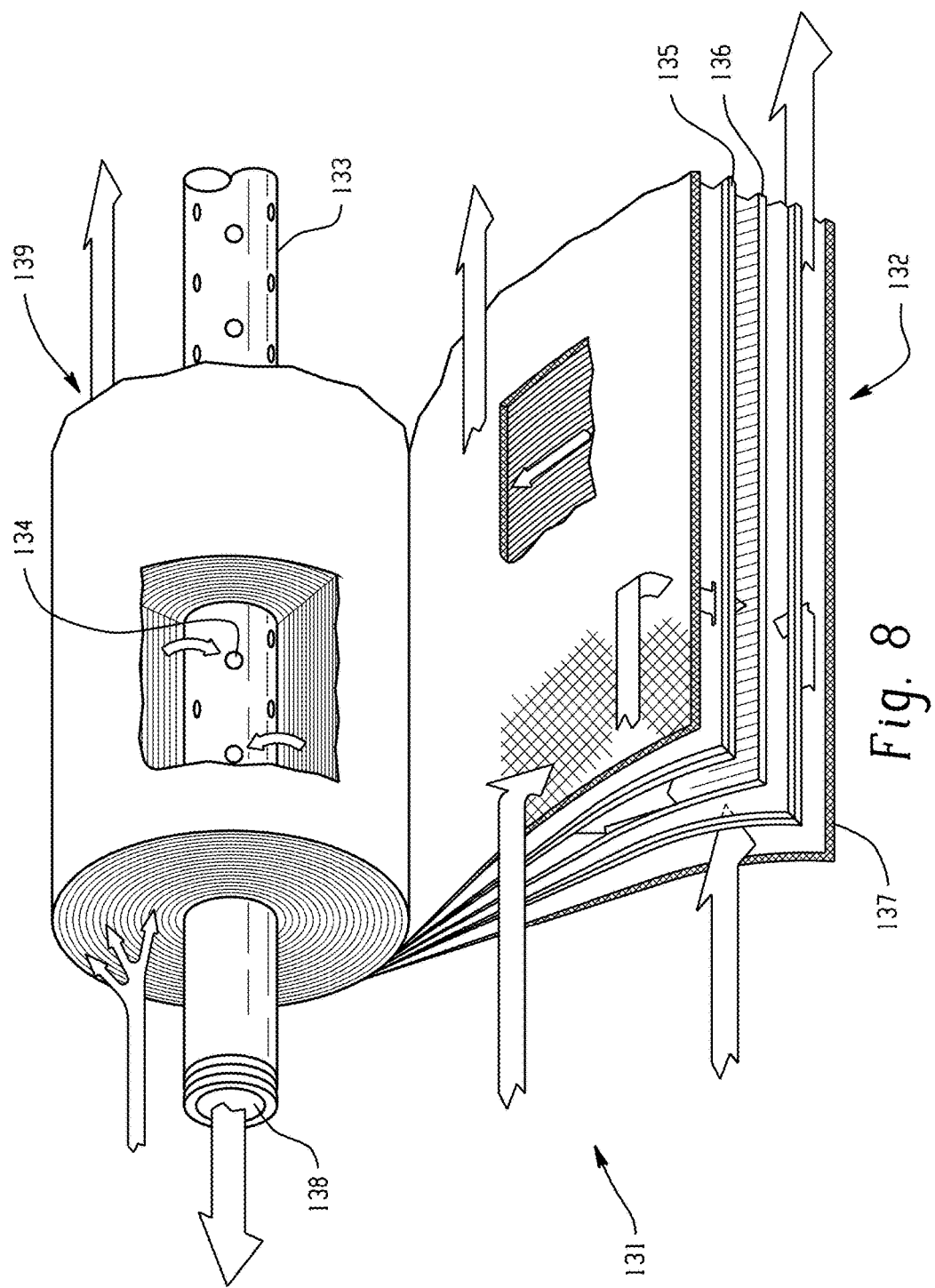
FIG. 8 shows an embodiment of a spiral wound separation module.

The separation module may have a spiral wound design, as shown in FIG. 8. A spiral wound separation module 131 may comprise a sheet of the asymmetric membrane 132 wound onto a hollow core member 133 having perforations 134. Alternatively, the hollow core member 133 may comprise a porous material. Additional layers, such as reinforcing layer 135, inner spacer 136, and outer spacer 137 are also provided. The permeated fluid passes through the perforations 134 in the hollow core member 133 and can be removed through the output 138 of the hollow core member 133. Retentate fluid passes through the outer spacer 137 and exits through the residual output 139.

Figure 9:
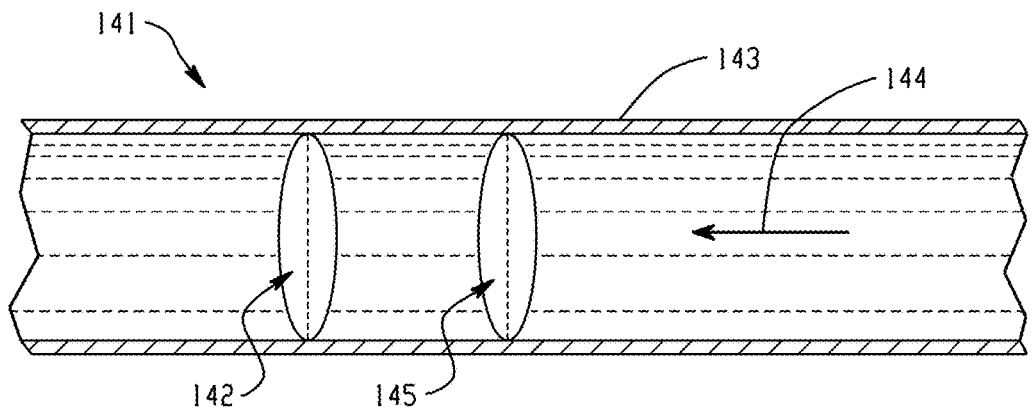
FIG. 9 shows an embodiment of a disk separation module.

The separation module may have a disk design, as shown in FIG. 9. A disk separation module 141 may comprise a filter 142 comprising the porous membrane disposed within a tube 143. The tube may comprise any suitable material, such as a material that is impermeable to the fluid. A support (not shown) may be optionally present. The fluid 144 may contact the disk at a selected pressure sufficient to cause the permeate to pass through the disk. In another embodiment, a plurality of disks may be used, for example to provide a prefilter 145. The prefilter 145 may be the same as or different than the filter 142. For example, the prefilter 145 may have larger pores than the filter 142, or the prefilter 145 may further comprise a functionalized surface, e.g., a surface having a catalyst disposed thereon. In another embodiment the prefilter 145 comprises the asymmetric membrane and the filter 142 comprises a different material.

The separation module can have a plate and frame design, as shown in the expanded view of FIG. 8. A filter plate of the separation module may comprise a base body 151, the asymmetric membrane 153, and a frame 155, wherein the frame 155 comprises an inlet 152 and an outlet 154. The asymmetric membrane is mounted on one or both sides of the base body and is held in place by a frame mounted in face to face contact with the asymmetric membrane to form the filter plate. The filter can have any suitable shape, and can be square, round, rectangular, or polygonal. The inlet and outlet allow entry of the input stream and exit of the permeate stream. An advantage of the plate and frame design is that the filter media used in making the filter plate assembly can be replaced when desired. The frame 155 and base body may comprise any suitable material, such as a metal, such as steel, or aluminum, or a polymer such as polypropylene or polyethylene. The frame 155 may be fabricated by a molding or a casting process and then machined to the desired size. Due to the solid nature of the frame 155, it can hold the asymmetric membrane 153 to the base body 151 tightly and provide a desirable sealing effect.

Figure 11:
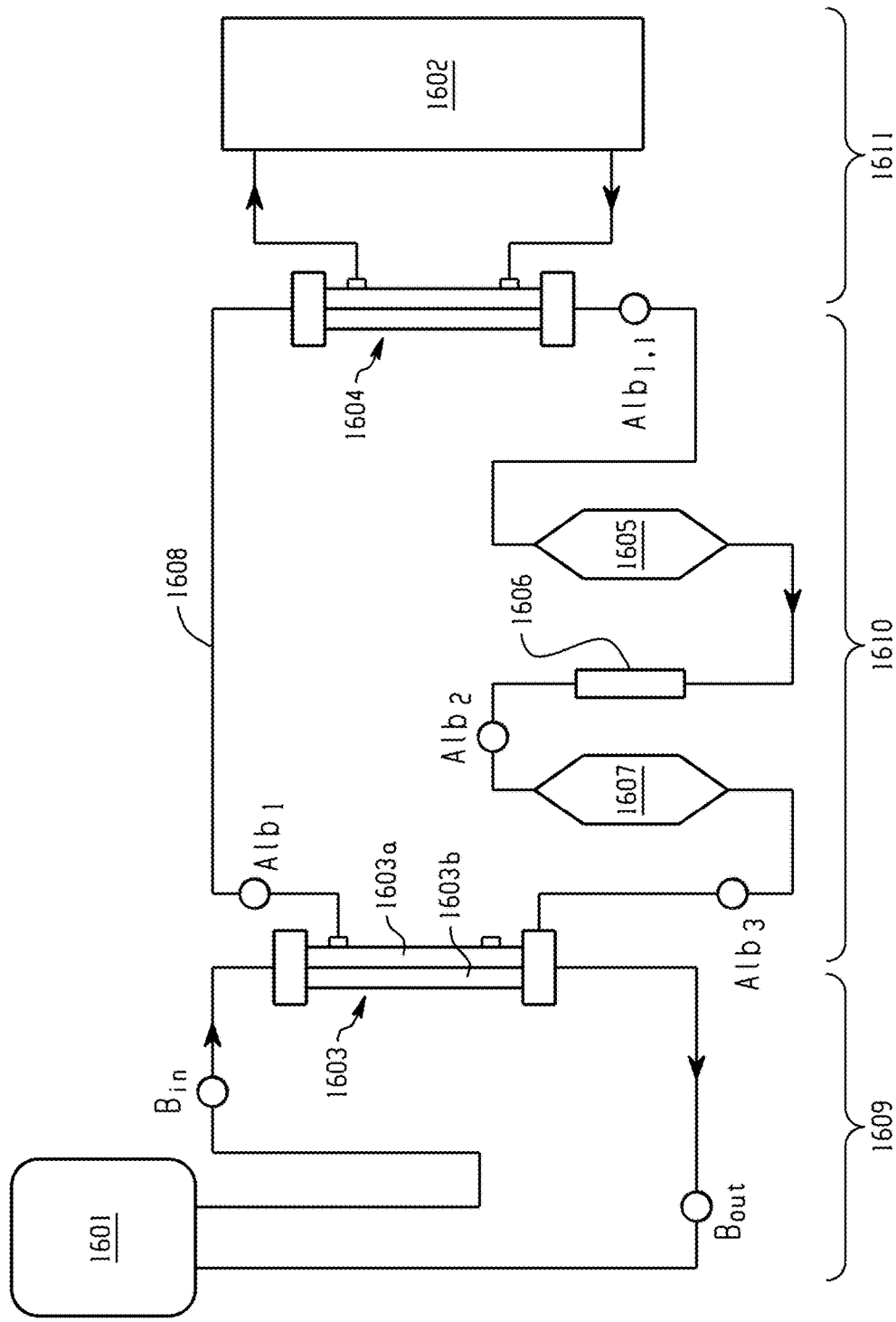
FIG. 11 shows an embodiment of a system for liver dialysis comprising a separation module for liver dialysis.

The porous membrane can be used for blood dialysis. In liver dialysis systems, blood is cleansed in an extracorporeal circuit that is a combination of both kidney and liver dialysis. In dialysis, blood is circulated through a module containing a dialysis solution to pass the blood across the porous membrane. A dialysis solution flows on opposite side of the porous membrane, and water and wastes, such as urea, uric acid, and creatine, move between these two solutions. The cleansed blood is then returned via the circuit back to the body. Disclosed in FIG. 11 is an embodiment of a separation module for liver dialysis and a system for liver dialysis comprising the module. The system comprises a blood circuit 1609, an albumin circuit 1610, and a dialysate circuit 1611. As shown in FIG. 9, the patient's blood is passed into a separation module 1603 comprising the porous membrane. The dialysate side 1603a of the separation module 1603 provides for clean human albumin that acts as a dialysate. As the patient's blood moves along the membrane, water-soluble and protein bound toxins in the blood are transported through the membrane and into the dialysate albumin solution on the other side 1608. The membrane is impermeable to albumin and to other valuable proteins such as hormones and clotting factors, keeping them in the patient's circulation. The cleansed blood then returns to the patient. Meanwhile, the albumin solution carrying the toxins is recycled by passing first through a low-flux dialyzer 1604 opposite a buffered aqueous solution 1602. This process is similar to that found in kidney dialysis and removes water-soluble substances from the albumin solution. The albumin then passes through an activated carbon adsorber 1605 and, after passing a filter 1606 which removes carbon particles, passes through an anion exchanger 1607 that removes toxins bound to albumin. The recycled albumin can then again enter the separation module 1603 and bind again to toxins which can thus be removed from the patient's blood.

Similar processes can be used to separate polysaccharides. In a method of separating of polysaccharides, the method may comprise contacting a mixture of sugars, such as dextrose, glucose, and fructose with the asymmetric membrane to separate the polysaccharides and provide a product stream enriched in a selected sugar.

Protein or enzyme recovery is also disclosed. A method for recovering a protein or enzyme of interest from a culture solution using cross-flow membrane filtration is provided, the method comprising: subjecting a culture solution comprising a protein or an enzyme of interest to cross-flow membrane filtration a conditions that cause the protein of interest to be retained in a feed stream to allow purification, concentration, and/or buffer exchange of the protein or enzyme of interest. Alternatively, the membrane allows the passage of the protein or enzyme of interest.

The production of purified water, e.g., drinking water, is also disclosed. Reverse osmosis membranes are designed to remove dissolved salts from water. Water passes readily through the reverse osmosis membrane, whereas dissolved salt is retained. Under natural conditions of osmosis, water will diffuse through a semipermeable membrane toward a region of higher salt concentration in order to equalize solution strength on both sides of the membrane. In order to overcome and reverse this osmotic tendency, pressure is applied to feedwater to force water to permeate from a region of higher salt concentration to lower salt concentration, thereby producing a purified stream.

Figure 10:
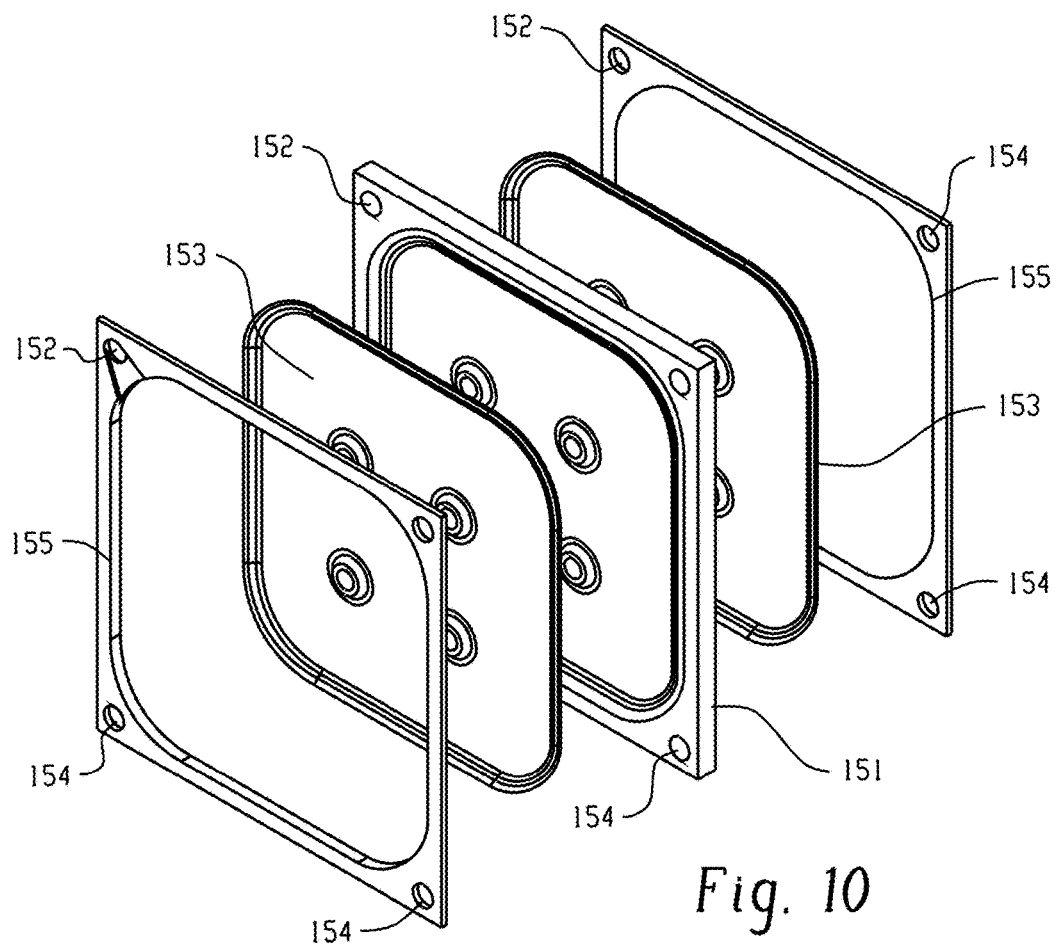
FIG. 10 shows an embodiment of a plate and frame separation module.
Figure 12:
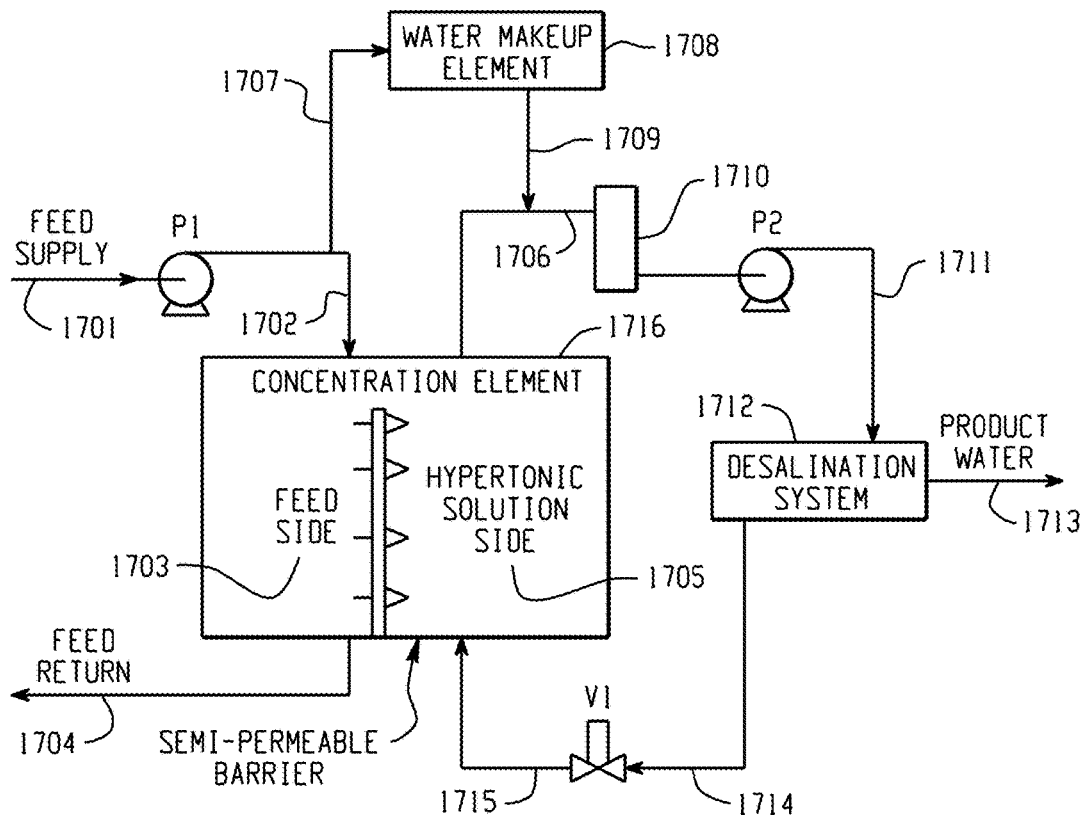
FIG. 12 shows an embodiment of a system for pretreatment of water.

The porous membrane can be used pretreatment of water in a desalination system, an embodiment of which is shown in FIG. 12. This pretreatment may remove or treat any solutes that may that may foul or scale the desalination system. A hypertonic solution can comprise a concentrated feed and its solute composition is the same as that in the feed. However, in a hypertonic solution, contamination components have been concentrated to a level higher than the feed. Additionally, in the hypertonic solution, any solutes that may foul or scale the desalination element can be removed or in some cases addressed by the introduction of anti-scale agents. The porous membrane separates the feed 1703 and the hypertonic solution 1705. In such an embodiment, water flows from the feed into the hypertonic solution across the membrane according to solute concentration gradients between the feed and the hypertonic solution. Thus, the feed water can be concentrated and the hypertonic solution can be diluted in a concentration module 1716 ("Concentration Element" in FIG. 12) which comprises the porous membrane. The hypertonic solution can then be re-concentrated in a desalination system by distillation, electrodialysis or otherwise and then recycled back into a concentration module comprising the porous membrane. As shown in FIG. 10, aqueous feed 1701 enters the system through pump P1 and exits by a discharge 1704. In the concentration module, the feed 1702 can be passed across one side of the porous membrane on the feed side 1703 of the concentration module. On the permeate side 1705 of the porous membrane is a hypertonic solution. The hypertonic solution can comprise feed water that has been concentrated to a level higher than the feed but lower than its solute solubility threshold. In the concentration module, water diffuses along concentration gradients from the higher water content feed 1703 through the membrane and into the lower water content hypertonic solution 1705. The feed 1702 is thereby concentrated and the hypertonic solution 1705 is thereby diluted in the concentration module 1716. Water can be removed from the hypertonic solution in the desalination system. This water 1713 becomes the final product of the desalination system. The hypertonic solution can be re-concentrated as a result of the removal of the water. This reconstituted hypertonic solution 1714 can be then passed through valve V1 and returned back 1715 to the hypertonic solution side 1705 of the concentration module, and the process can be repeated. Lost solute can be made-up by diverting a constant flow of feed water 1707 back into the hypertonic solution 1709. After mixing the feed makeup 1709 with the hypertonic solution 1706, the resulting solution can be passed into a permeate holding tank 1710. From tank 1710 the fluid can then be pumped by P2 via 1711 into the desalination system 1712.

Similarly, the separation module can be used to remove contaminants, including biological contaminants such as bacteria or protozoa, or organic contaminants, such as organic compounds such as polychlorinated biphenyls (PCBs), to produce a purified product stream.

The membrane and separation module thereof can also useful for oxygenation of blood, such as in an artificial lung device. An artificial lung device contains a dialyzer module comprising the membrane interposed in the blood circulation of a patient whose normal respiration has been interrupted, for example, while undergoing heart surgery. Blood circulates through the dialyzer module which includes the membrane separating the blood from a suitable oxygen-bearing gas or solution. The membrane is impermeable to liquid but allows carbon dioxide to pass from the blood and oxygen to pass to the blood.

Figure 13:
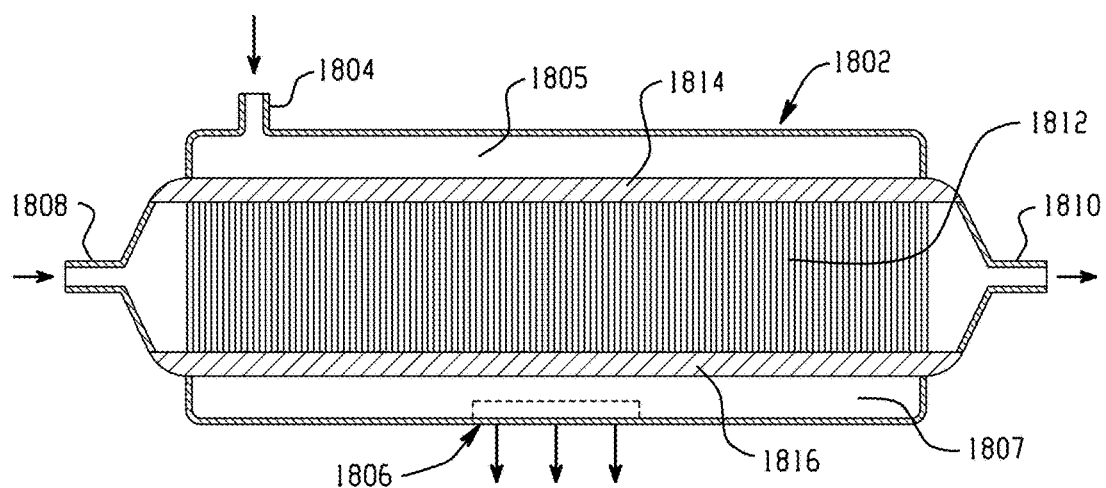
FIG. 13 shows an embodiment of a blood oxygenator.

An embodiment of the blood oxygenator is shown in FIG. 13. A suitable housing 1802, in the form shown, has a generally rectangular cross-sectional configuration and is provided with an array of hollow fibers 1812 of the porous membrane. In the form shown the fibers are positioned generally vertically and have their ends secured to a sealing material 1814 (top) and 1806 (bottom). The sealing material can comprise a thermoplastic or a thermoset, such as epoxy, silicone rubber, or polyurethane. The fibers 1812 can have a length substantially less than the longitudinal extent of the housing. The ends of the fibers 1812 project through the upper and lower extremities respectively of the sealing material 1814 and 1806. In this fashion, the gas inlet 1804 which is in communication with inlet chamber 1805 is also in communication with the open ends of the fibers 1812 thereby permitting oxygen to be introduced through the gas inlet 1804 and into the fibers 1812 for flow downward therethrough. Similarly, the lower ends of the fibers 1812 are in communication with the gas outlet 1806 through outlet chamber 1807. Blood entering the oxygenator through blood inlet 1808 will flow generally from one end of the oxygenator to the other and emerge through blood outlet 1810. In flowing through the oxygenator, the blood flows in a direction which is generally transverse to and substantially perpendicular to the axial orientation of the fibers.

Figure 15:
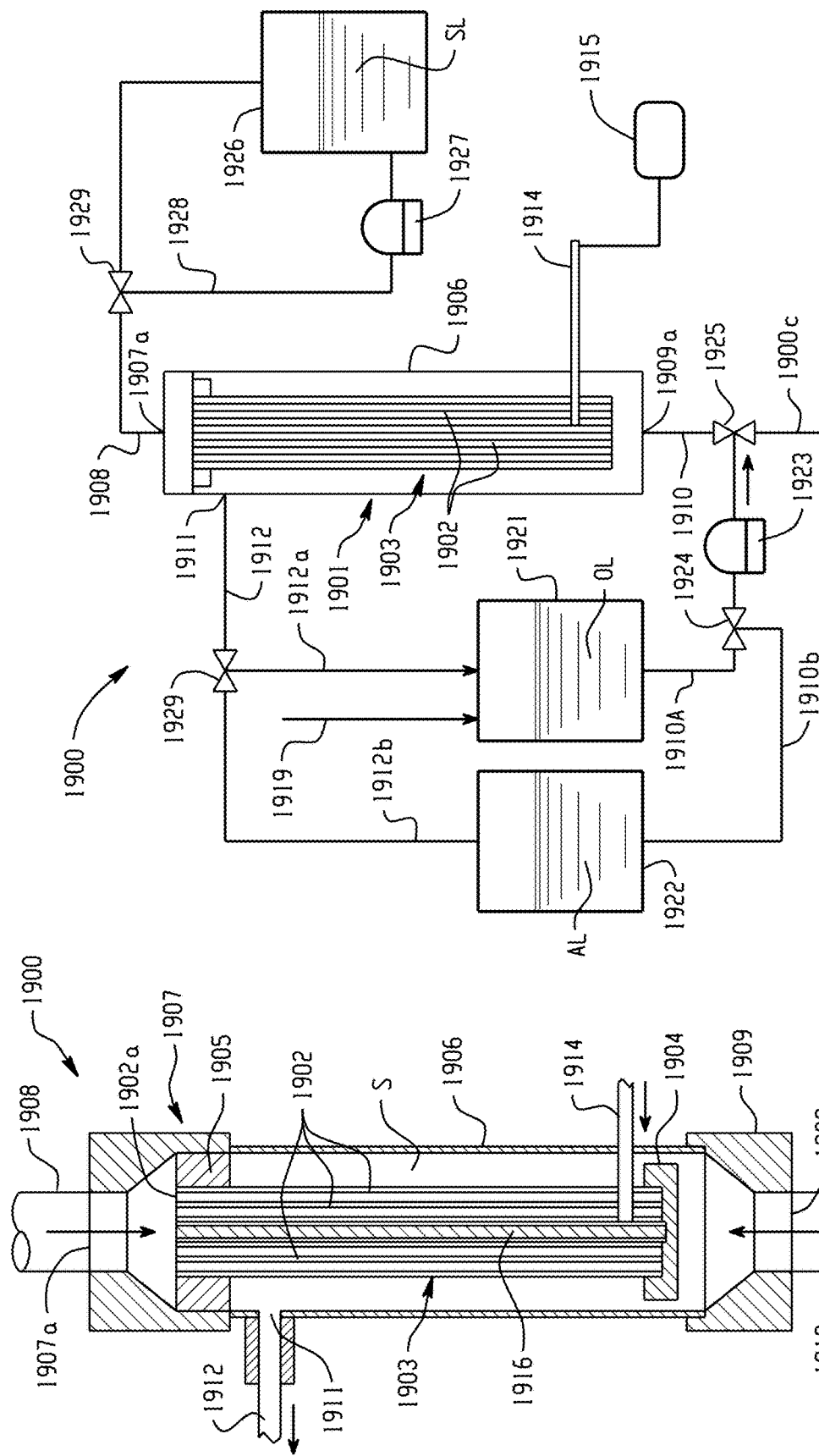
FIG. 15 shows an embodiment of a system for treatment of oil-containing wastewater treatment, containing the separation module of FIG. 14.
Figure 14:
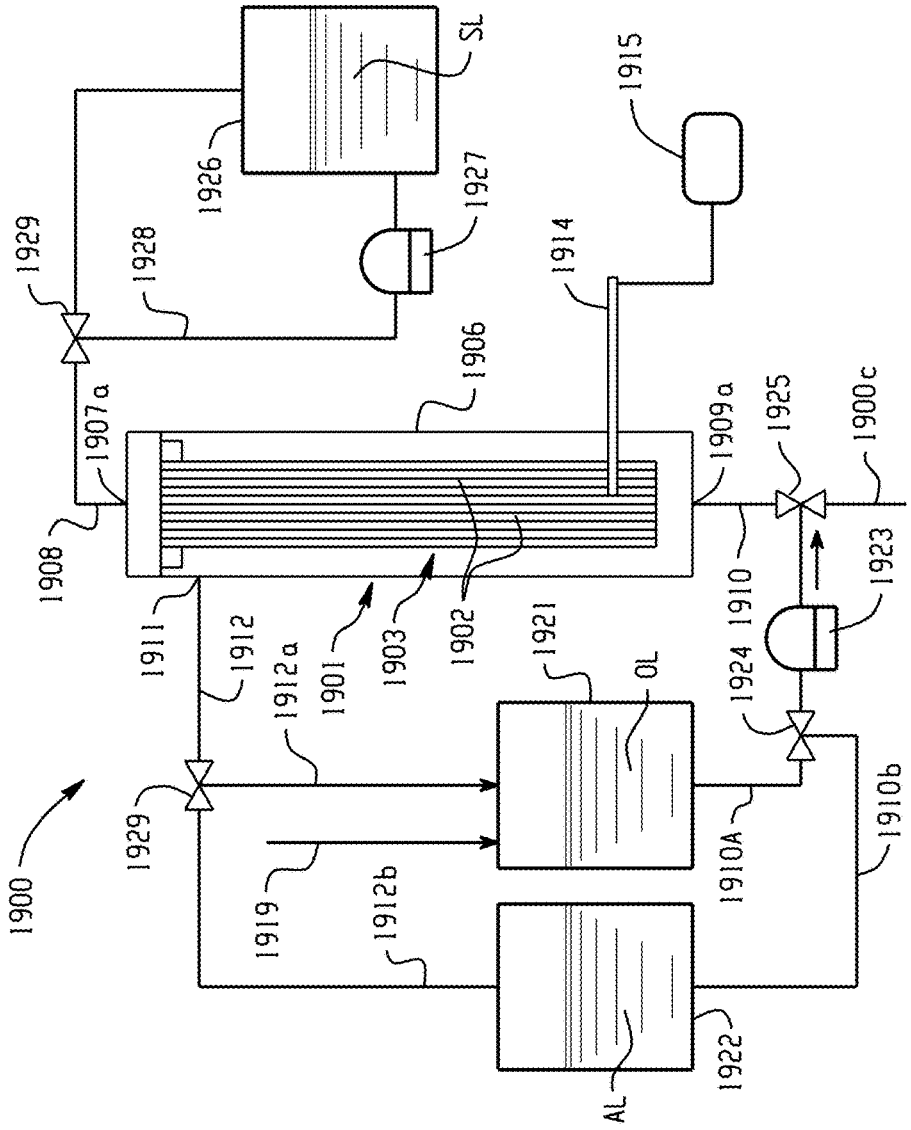
FIG. 14 shows an embodiment of a separation module for treatment of oil-containing wastewater.

The porous membrane is also useful for wastewater treatment. An embodiment of a separation module for treatment of oil-containing wastewater is shown in FIG. 14, and a system for wastewater treatment comprising the separation module for oil-containing wastewater treatment is shown in FIG. 15. The separation membrane module 1900 includes an assembly 1903 in which a plurality of hollow fibers 1902 are bundled together, the lower end of the assembly 1903 is sealed with a sealing member 1904, and a lower open end of each hollow fiber 1902 is closed. The upper end of the assembly 1903 is sealed with a fixing member 1905 with an upper open end 1902a of each hollow fiber membrane 1902 protruding through the sealing member 1905. The assembly 1903 is housed in an external cylinder 1906. An upper cap 1907 is attached by bonding to the upper end of the external cylinder 1906. An outlet port 1907a is provided such that the inside of the upper cap 1907 communicates with the hollow portion of each hollow fiber membrane 1902, and the outlet port 1907a is connected to an outlet pipe 1908 for taking out treated water. A lower cap 1909 is fixed by bonding to the lower end of the external cylinder 1906. An inlet port 1909a for liquid to be treated, i.e., oil-containing wastewater, is provided on the lower cap 1909, and the inlet port 1909a is connected to an inlet pipe 1910 which introduces the water to be treated. A space S is secured between the sealing member 1904 at the lower end of the assembly 1903 and the inner wall of the external cylinder 1906 so that oil-containing wastewater introduced from the inlet port 1909 a can promptly flow into the assembly 1903 inside the external cylinder 1906. Furthermore, a discharge port 1911 for non-filtered, untreated water is provided at the peripheral wall in the vicinity of the upper end of the external cylinder 1906, and the discharge port 1911 communicates with a circulation pipe 1912. Furthermore, the upper fixing member 1905 and the lower sealing member 1904 are joined by a reinforcing bar 1916 at the center. The reinforcing bar 1916 prevents the non-rigid hollow fiber membranes 1902 from being lifted by the force of stream of oil-containing wastewater from the lower part and is provided to secure verticality.

Regarding the system for wastewater treatment as shown in FIG. 15, system 1900 includes an oil-containing wastewater storage tank 1921 into which oil-containing wastewater OL is continuously poured from a pipe 1919, a cleaning liquid storage tank 1922 which stores a cleaning liquid composed of an alkaline aqueous solution (hereinafter referred to as an "alkaline cleaning liquid") AL, the inlet pipe 1910 through which each of the oil-containing wastewater storage tank 1921 and the cleaning liquid storage tank 1922 communicates with an inlet portion 1909a for water to be treated of the separation module 1901, and which is inserted with a pump 1923 and a switching valve 1924, and the circulation pipe 1912 through which each of the oil-containing wastewater storage tank 1921 and the cleaning liquid storage tank 1922 communicates with the discharge port 1911 for non-filtered, untreated liquid of the separation membrane module 1901. The inlet pipe 1910 is provided with the switching valve 1924 on the upstream side of the pump 1923, and the pipe is branched by the switching valve 1924. A branch pipe 1910A is connected to the oil-containing wastewater storage tank 1921, and a branch pipe 1910B is connected to the cleaning liquid storage tank 1922. Furthermore, the inlet pipe 1910 is connected to a discharge pipe 1910C for backwash water through a switching valve 1925 on the downstream side of the pump 1923. The circulation pipe 1912 serving as a cleaning liquid path is also branched. A branch pipe 1912A is connected to the oil-containing wastewater storage tank 1921, and a branch pipe 1912B is connected to the cleaning liquid storage tank 1922. Furthermore, by inserting a switching valve 1929 at the branching position, a non-filtered, untreated liquid is returned to the oil-containing wastewater storage tank 1921, and the alkaline cleaning liquid is returned to the cleaning liquid storage tank 1922 for circulation during alkali cleaning. The outlet pipe 198 which is connected to the outlet port 197a for filtered, treated liquid SL and takes out treated liquid is connected to a treated liquid storage tank 1926. At the same time, since the treated liquid stored in the treated liquid storage tank 1926 is used as backwash water, a backwash pipe 1928 inserted with a backwash pump 1927 is connected between the treated liquid storage tank 1926 and the outlet pipe 198. A diffusion air inlet pipe 1914 is connected to a blower 1915 inserted into the pipe 1910 close to the inlet port 1936a of the separation membrane module 1931, and thereby, diffusion air is fed into the hollow fiber membranes 1932.

Figure 16:
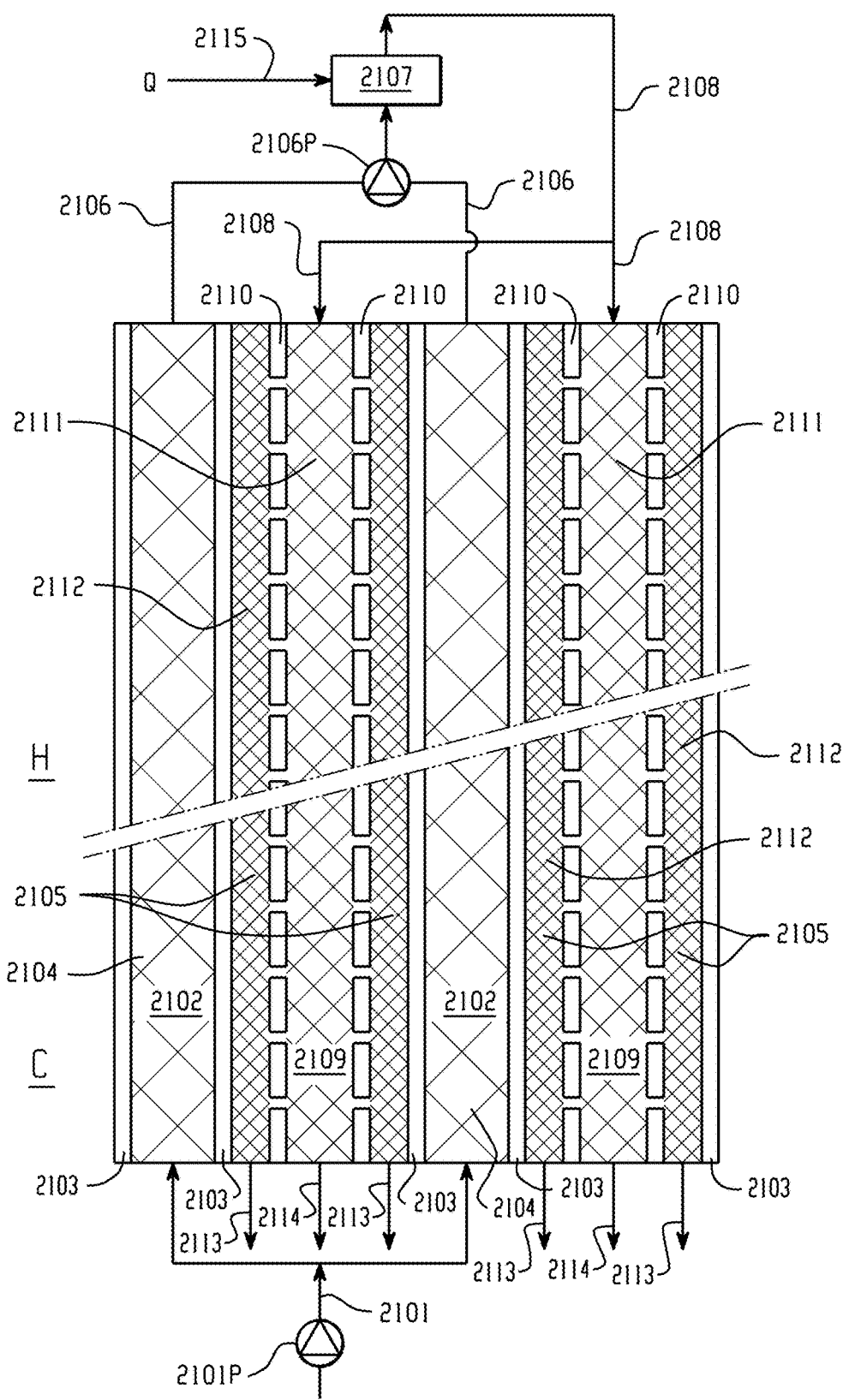
FIG. 16 shows an embodiment of a module for membrane distillation.

The porous membrane can be used for membrane distillation. The method of membrane distillation includes passing a heated vaporizing stream of a liquid through a porous membrane, whereby a vapor of the liquid flows via the pores of the membrane to the other side of the membrane, and condensing the vapor on the other side of the membrane to give a distillate stream. An embodiment of a module for membrane distillation is shown in FIG. 14. As shown in FIG. 16, the module is divided into a cold side C and a hot side H. A relatively cold feed stream 2101 is pumped with feed pump 2101P into the parallel feed channels 2102, at the cold side C. These feed channels are constructed of non-porous walls 2103 and a spacer material 2104. In feed channels 2102, the feed stream is heated by taking up heat from the warmer distillate channels 2105 at the other side of the walls 2103. Thus, gradually the feed stream becomes hotter and leaves the separation module as stream 2106 at the hot side H, with the aid of pump 2106P. This pump ensures by suction that the pressure in the feed channels 2102 is relatively low; for example between 0.1 and 3.0 bar (absolute pressure). The relatively hot feed stream 2106 is pumped into a heat exchanging device 217, where it is heated further by an external heat input 2115, (the heat used can be waste heat, solar heat, steam, hot solid material, etc.), and leaves the device as relatively hot retentate stream 2108. Stream 2108 enters the module at the hot side H, and flows through the parallel placed retentate channels 2109 in more or less counter-current flow with stream 2101. The retentate channels 2109 are constructed of porous membranes 2110 and the spacer material 2111. In these retentate channels, the retentate stream 2108 gradually becomes cooler because of evaporation of water vapor, and some heat conduction, through the porous membranes 2110 into the distillate channels 2105, where the water vapor condenses forming a pure, water distillate 2113. The distillate channels are delimited by the porous membrane 2110 at one side and a non-porous condenser wall 2103 at the other side. A spacer material 2112 can be optionally disposed inside channels 2105. The released heat in the distillate channels 2105 is primarily transferred through inner walls 2103 into the feed stream 2101, flowing in the feed channels 2102. The liquid distillate leaves the module preferably at the cold side C, by which also heat of stream 2113 is recovered and transferred into stream 2101. It can, however, also be discharged at both sides C and H of the module. This discharge can take place by gravity, pumping, and/or by pressure build up inside channels 2105 as a result of the water produced. The relatively cool and concentrated retentate stream leaves the module at the cold side C as stream 2114. For a large part of the separation module, especially the hot side H, the absolute liquid pressure inside the retentate channels 2109 is higher than in the corresponding feed channels 2102. The absolute liquid pressures in the retentate channels can range between 1.0 and 4.0 bar, for example.

In addition, the separation module can be useful for separating gases and/or vapors from mixtures of liquids or mixtures of liquids gases using the membrane separation processes of membrane stripping, membrane distillation. In membrane stripping, a material permeating through or across the membrane is removed from the module as a gas or a vapor. In membrane distillation, a membrane is used and the material permeating through or across the membrane is condensed and removed from the device as a liquid.

Since a separation module fabricated from the porous membrane is useful for a wide variety of aqueous fluid separation applications in many different fields as described above, it can be applicable to other fluid separation problems not expressly disclosed herein.

Advantageously, any of the separation modules and devices comprising the separation modules as described herein, can be connected to a computer network. For example, a dialysis device for conducting hemodialysis on a patient suffering from renal failure can be remotely controlled through a computer network. In particular, a dialysis system can include a controller that controls a dialysis device, to carry out a hemodialysis treatment. The controller receives signals from the dialysis device that indicate states of the device, and provides instructions that control the device. The controller connects to a proxy server through a network. The proxy server provides a virtual control, reflecting the controller of the hemodialysis device to a server through the network. A client device can connect to the server through the network to receive the information from the proxy server so that an operator can see the virtual control from the client device. Thus, the operator can control the dialysis device remotely, monitoring the operation of the dialysis device and also providing instructions to the dialysis device through the proxy server via the network and server. The dialysis device can also include video and audio transmission capabilities, through which a patient can communicate with the operator controlling the hemodialysis device at the client device through streaming video and audio. For example, both the dialysis device and the client device can have video cameras, which can allow the patient to see the operator on a screen of the dialysis device, and the operator to see the patient on a screen of the client device. The dialysis device can include multiple cameras to send video information showing various connections between the patient and the dialysis device and between components on the dialysis device. The dialysis device can also include an internet protocol (IP) phone through which the dialysis device can transmit voice data to the client device.

Figure 17:
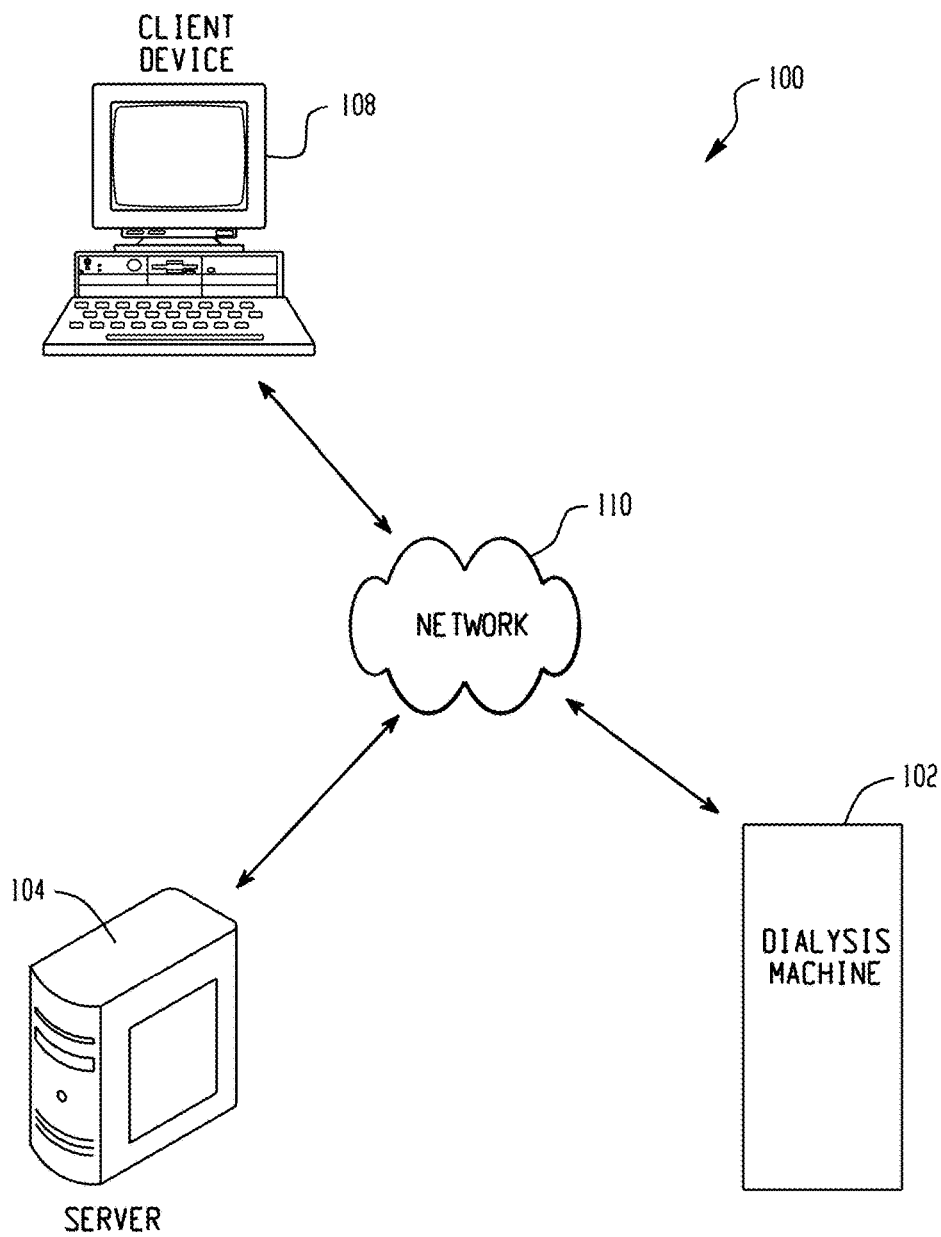
FIG. 17 is a schematic diagram of a remote control dialysis system 100 including a dialysis device 102 that is configured to connect to a server 104 through a network 110.

Referring now to FIG. 17, a remote control dialysis system 100 includes a dialysis device 102 ("dialysis machine" in FIG. 17) that is configured to connect to a server 104 through a network 110. The server 104 generates a proxy for the dialysis device 102 and a virtual controller for the dialysis device 102. A client device 108 connects to the server 104 through the network 110. The dialysis device 102 communicates with the proxy on the server 104 to provide information about operations on the dialysis device 102. The server 104 provides the information from the proxy to the client device 108. A remote operator at the client device 108 thus receives information from the dialysis machine 102, and monitors the operation of the dialysis machine 102. The remote operator also provides instructions through the client device 108 to the dialysis device 102. The instructions input by the remote operator are sent to the server 104 through the network 110. The server 104 relays the instructions through the proxy to the dialysis device 102 for execution.

Thus a system comprises: a server; a dialysis device for conducting hemodialysis on a patient suffering from renal failure, the device comprising the separation module comprising a hollow fiber or bundle of hollow fibers as described herein, configured to connect to the server through a network; and a client device also configured to connect to the server through the network, wherein the server is configured for: maintaining an access control list to determine whether the client device is authorized to connect to the device; and providing a connection for transfer of data between the dialysis device and the client device. In some embodiments of the system, the server is further configured for: receiving a request for a network connection from the dialysis device; establishing the network connection with the dialysis device; receiving, from the client device, a request to access the dialysis device; authorizing the client device to access the dialysis device; receiving from the dialysis device information pertaining to operation of the dialysis device; and providing to the client device the information. In some embodiments, the dialysis device and client device are at a first location, and the server is at a remote location relative to the first location. Further details of the system can be found in U.S. Patent Publication No. 2016/0021101, of Wang et al., which is incorporated herein in its entirety. A clinical data management system for handling patient-related information and a monitoring system for monitoring a plurality of hemodialysis devices as disclosed herein and for managing a plurality of device-related data records as a function of the respective type of device is disclosed in U.S. Patent Publication No. 2016/0022892 of Eifler et al., which is incorporated herein in its entirety.

This disclosure is further illustrated by the following embodiments, which are not intended to limit the claims.

Embodiment 1

A separation module comprising a porous membrane comprising, consisting essentially of, or consisting of a poly(phenylene ether) copolymer comprising 10 to 40 mole percent repeat units derived from 2-methyl-6-phenylphenol and 60 to 90 mole percent repeat units derived from 2,6-dimethylphenol; and a block copolymer comprising backbone or pendant blocks of poly($C_{2-4}$ alkylene oxide).

Embodiment 2

The separation module of embodiment 1, wherein the block copolymer is a poly(ethylene oxide)-poly(propylene oxide)-poly(ethylene oxide) block copolymer, a poly(ethylene oxide)-poly(propylene oxide)-poly(ethylene oxide) block copolymer, a poly($C_{2-4}$ alkylene oxide)-poly(dimethylsiloxane) block copolymer, or a combination comprising at least one of the foregoing.

Embodiment 3

The separation module of embodiment 1 or 2, wherein the porous membrane comprises 20 to 90 weight percent of the poly(phenylene ether) copolymer, and 10 to 80 weight percent of the block copolymer, based on the total weight of the porous membrane.

Embodiment 4

The porous membrane of any of embodiments 1-3, wherein the block copolymer comprises: a poly(ethylene oxide)-poly(propylene oxide)-poly(ethylene oxide) block copolymer having a number average molecular weight of 1,000 to 14,000 daltons, and comprising, based on the weight of the block copolymer, 1 to 90 weight percent, of poly(ethylene oxide) blocks; a poly(propylene oxide)-poly(ethylene oxide)-poly(propylene oxide) block copolymer having a number average molecular weight 500 to 12,000 daltons, and comprising, based on the weight of the block copolymer, 1 to 90 weight percent of poly(ethylene oxide) blocks; or a combination comprising at least one of the foregoing.

Embodiment 5

The separation module of any of embodiments 1-3, wherein the block copolymer comprises a poly($C_{2-4}$ alkylene oxide)-poly(dimethylsiloxane) block copolymer comprising 5 to 60 weight percent polysiloxane, and having a number average molecular weight of 500 to 14,000 daltons.

Embodiment 6

The separation module of any of embodiments 1-5, wherein the porous membrane is a flat sheet.

Embodiment 7

The separation module of embodiment 6, wherein the flat sheet is in a spiral-wound configuration.

Embodiment 8

The separation module of embodiment 6, wherein the flat sheet is in a plate and frame configuration.

Embodiment 9

The separation module of any of embodiments 1-5, wherein the porous membrane is in a capillary or tubular configuration.

Embodiment 10

The separation module of any of embodiments 1-5, wherein the porous membrane is a hollow fiber.

Embodiment 11

The separation module of embodiment 10, wherein the separation module comprises: an enclosure configured to contain a bundle of the hollow fibers, the enclosure having an outlet configured for withdrawing a permeate fluid; a first encasement comprising a thermoset or a thermoplastic polymeric material and located at a first end of the bundle, arranged such that the hollow fiber membranes are embedded in the first encasement and communicate through the first encasement and are open on an outer face of the first encasement; a second encasement comprising a thermoset or a thermoplastic polymeric material and located at a second end of the bundle opposite the first end of the bundle, arranged such that the hollow fiber membranes are embedded in the second encasement and communicate through the second encasement and are open on an outer face of the second encasement; a first end cap arranged and configured for attaching and sealing to the first end of the bundle or enclosures at or near the first encasement; a second end cap arranged and configured for attaching and sealing to the second end of the bundle or enclosures at or near the second encasement; an inlet for introducing a fluid mixture to be separated into bores of the hollow fiber membranes at the first encasement; and an outlet for withdrawing a retentate fluid from the bores for the hollow fiber membranes at the second encasement.

Embodiment 12

A device for wastewater treatment, water purification, desalination, or separating water-insoluble oil from oil-containing wastewater, the device comprising the separation module of any of embodiments 1-11.

Embodiment 13

A device for purification of a liquid by membrane distillation comprising the separation module of any of embodiments 1-11.

Embodiment 14

A device for sugar purification, protein concentration, or enzyme recovery, comprising the separation module of any of embodiments 1-11.

Embodiment 15

A dialysis device for conducting hemodialysis on a patient suffering from renal failure, the device comprising the separation module of embodiment 10 or 11.

Embodiment 16

A dialysis device for conducting liver dialysis on a patient suffering from liver failure, the device comprising the separation module of embodiment 10 or 11.

Embodiment 17

A blood oxygenator comprising the separation module of embodiment 10 or 11.

Embodiment 18

A system comprising: a server; the dialysis device of embodiment 15 configured to connect to the server through a network; and a client device also configured to connect to the server through the network, wherein the server is configured for: maintaining an access control list to determine whether the client device is authorized to connect to the device; and providing a connection for transfer of data between the dialysis device and the client device.

Embodiment 19

The system of embodiment 18, wherein the server is further configured for: receiving a request for a network connection from the dialysis device; establishing the network connection with the dialysis device; receiving, from the client device, a request to access the dialysis device; authorizing the client device to access the dialysis device; receiving from the dialysis device information pertaining to operation of the dialysis device; and providing to the client device the information.

Embodiment 20

The system of embodiment 18 or 19, wherein the dialysis device and client device are at a first location, and the server is at a remote location relative to the first location.

The invention is further illustrated by the following non-limiting examples.

Preparative Example 1: Synthesis of MPP-DMP Copolymer 2,6-Dimethylphenol (DMP) of very high purity, >99.5%, was purchased from Sigma-Aldrich. 2.-Methyl-6-phenyl-phenol (MPP) can be prepared via a modification of the established high-temperature alkylation process used to prepare DMP wherein o-phenyl phenol (OPP) is used as the starting material instead of phenol. The copolymerization was conducted in a one-gallon steel bubbling reactor, equipped with a stirrer, temperature control system, nitrogen padding, oxygen bubbling tube, and computerized control system. There were also a feeding pot and a pump for dosing reactants into the reactor. Raw materials used in the copolymerization are included in Table 2.

TABLE 2

Materials

| Abbreviation | Chemical Name |
|---|---|
| DMP | 2,6-Dimethylphenol, >99.5 wt. %, available from Sigma-Aldrich. |
| MPP | 2-Methyl-6-phenylphenol |
| DBA | Di-n-butylamine |
| DBEDA | N,N'-Di-tert-butylethylenediamine |
| DMBA | N,N-Dimethylbutylamine |
| QUAT | Didecyldimethyl ammonium chloride |
| NTA | Nitrilotriacetic acid |
| CAT | Solution of $Cu_2O$ in concentrated HBr, 6.5 wt. % Cu |
| NMP | N-Methyl-2-pyrrolidone, available from ThermoFisher. |
| MPP-DMP Copolymer | Poly(2-methyl-6-phenyl-1,4-phenylene-co-2,6-dimethyl-1,4-phenylene), prepared as described herein. |
| EO | Ethylene oxide repeat unit (—$CH_2CH_2O$—) |
| PO | Propylene oxide repeat unit (—$CH_2CH(CH_3)O$—) |
| PEO | Poly(ethylene oxide) block |
| PPO | Poly(propylene oxide) block |

Reactor charges and continuous monomer feed solution composition are shown in Table 3. The target mole fraction of MPP was 0.2. After charging the reactor, the reactor contents were brought to 25° C. with stirring, and a continuous feed of monomer in toluene and then oxygen were begun. The monomer/toluene mixture was fed over 45 minutes, and oxygen feed was maintained until 130 minutes. The reactor temperature was ramped to 45° C. at 90 minutes and then ramped to 60° C. at 130 minutes. The reaction contents were then transferred to a separate vessel for addition of NTA to chelate the copper. The resulting mixture was stirred at 60° C. for 2 hours, and the layers were then allowed to separate. The decanted light phase was precipitated in methanol, filtered, reslurried in methanol, and filtered again. The MPP-DMP copolymer was obtained as a dry powder after drying in a vacuum oven under nitrogen blanket at 110° C. The MPP-DMP copolymer had an intrinsic viscosity (IV) was 1.3 deciliters per gram (dL/g), as measured in $CHCl_3$ solution at 25° C., using an Ubbelohde viscometer. The MPP-DMP copolymer also had a number average molecular weight ($M_n$) of 39,590 daltons, a weight average molecular weight ($M_w$) of 274,700 daltons, and a polydispersity of 6.9

TABLE 3

Material Amounts for Preparative Example 1

| Raw Material (g) | Example 1 |
|---|---|
| MPP/DMP (mole ratio) | 20/80 |
| CAT | 17.3 |
| DBEDA | 5.3 |
| DBA | 9.9 |
| DMBA | 34.3 |
| QUAT | 1.6 |
| DMP/TOLUENE 50/50 | 29.5 |
| TOLUENE | 2961.0 |
| MPP | 5.6 |
| Continuous Feed Solution (g) | |
| DMP/TOLUENE 50/50 | 364.5 |
| MPP | 69.4 |
| Total | 3498.36 |

Examples 1-3: Dense Films Cast from Chloroform Solution

Dense films were cast from chloroform solutions of the 20/80 poly(2-methyl-6-phenyl-1,4-phenylene ether-co-2,6-dimethyl-1,4-phenylene) copolymer of Preparative Example 1, and the poloxamers listed in Table 4, in a 4:1. Chloroform ($CHCl_3$) was chosen as the solvent, since it evaporates quicker than N-methyl-2-pyrrolidone (NMP). Films were cast on a glass plate using a 0.3-µm casting knife. Residual chloroform was evaporated in a nitrogen box for at least 16 hours.

The interactions between the MPP-DMP copolymer of and poloxamers were investigated by means of glass transition temperature ($T_g$) measured by differential scanning calorimetry (DSC) using a PerkinElmer DSC8000 instrument. The measurements were performed at a heating rate of 20° C. $min^{-1}$. The intrinsic hydrophilicity of the homogenous polymer films was measured by means of water contact angle. The optical contact angle measurements were performed on an OCA15 Plus from Dataphysics Instruments. The contact angle of a sessile drop of 2 µl water on the appropriate polymer film was measured six times for each coating (at room temperature), and the average and standard deviation are reported. The contact angles were measured ten seconds after the drop of water had been in contact with the surface.

TABLE 4

Polymer compositions used to prepare dense films cast from $CHCl_3$

| Ex. | Block Copolymer | Weight Ratio[a] | Tg (°C.) | Film Appear. | Contact Angle[b] (°) |
|---|---|---|---|---|---|
| Comp. 1 | No block copolymer | 100/0 | 210 | Clear | 79.0 ± .5 |
| 1 | L81: PEO—PPO—PEO 10% PEO, $M_n$ ~2,800 Da | 80/20 | 186 | Cloudy | 36.3 ± 2.4 |
| 2 | 31R1: PPO—PEO—PPO 10% PEO, $M_n$ ~3,300 Da | 80/20 | 182 | Cloudy | 27.9 ± 4.1 |
| 3 | P123: PEO—PPO—PEO 30% PEO, $M_n$ ~5,800 Da | 80/20 | 195 | Cloudy | 88.1 ± 1.8[c] |

[a]Weight ratio of 20/80 MPP-DMP copolymer to block copolymer.
[b]Top surface.
[c]Contact angle of bottom surface = 14.9 ± 3.9°.

As can be seen from Table 4, the films made from a 4:1 blend of 20/80 MPP-DMP copolymer with L81 or 31R1 (Examples 1 and 2) show significant reduction in contact angle compared to the PPE only film of Comparative Example 1. Surprisingly low contact angles of around 30° C. were observed even though L81 and 31R1 have relatively low PEO content of 10 wt. %. These data suggest that the poloxamers, or at least the hydrophilic PEO blocks of the poloxamers, orient themselves to the surfaces of the dense films.

In Example 3, the film made with P123, the contact angle was dependent on the side of the membrane which was tested. On the top side which had been in contact with air the contact angle was comparable to Comparative Example 1, made without block copolymer, while on the bottom side in contact with the glass plate, a very low contact angle of 14.9° C. was observed. It is hypothesized that during the relative slow evaporation of the chloroform, phase separation of the P123 and MPP-DMP copolymer (or chloroform) occurs, and P123 migrates to the bottom side in contact with the glass. For Examples 1 and 2, the contact angles are comparable on the top and bottom sides of the films. The fact that the asymmetry in contact angles is only observed for P123 and not for the other two poloxamers suggests a correlation with the higher PEO content of P123 (30 wt. % vs. 10 wt. % in L81 and 31R1.

Fourier Transform Infrared (FTIR) spectroscopy was used to characterize the dense films and porous membranes. The analysis was done on an ALPHA FTIR spectrometer from Bruker. Spectra were collected in the wave number range of 400 cm$^{-1}$ to 4000 cm$^{-1}$ at a resolution of 4 cm$^{-1}$ for a total of 60 scans per measurement. Attenuated total reflection (ATR) mode was utilized specifically analyze the surfaces of the films. For all films containing poloxamers (Examples 1-3), a clear C—O stretch peak is observed at 1110 cm$^{-1}$ in the ATR-FTIR spectra of the film surfaces. These spectra are reproduced in FIG. 1, with Examples 2, 1, 3, and Comparative Example 1 arranged from top to bottom.

Examples 4-6: Porous Membranes Cast from NMP and Water

Porous membranes were cast from dope solutions of 14 wt. % of the 20/80 MPP-DMP copolymer of Preparative Example 1, and 3.6 wt. % poloxamer in NMP (7:5, or 1.4:1 weight ratio of MPP-DMP copolymer to poloxamer. For each dope solution the solution viscosity was measured at 20-80° C. at different shear rates with a HAAKE™ VISCOTESTER™ 550 Rotational Viscometer (Table 5) and all of the solutions showed a fairly high viscosity. There was little difference between the normal and reversed block copolymer structures of additives L81 and 31R1, and a trend to slightly higher viscosity with increased PEO content of additive P123.

TABLE 5

Polymer dope solutions in NMP for porous membrane casting

Figure 3:
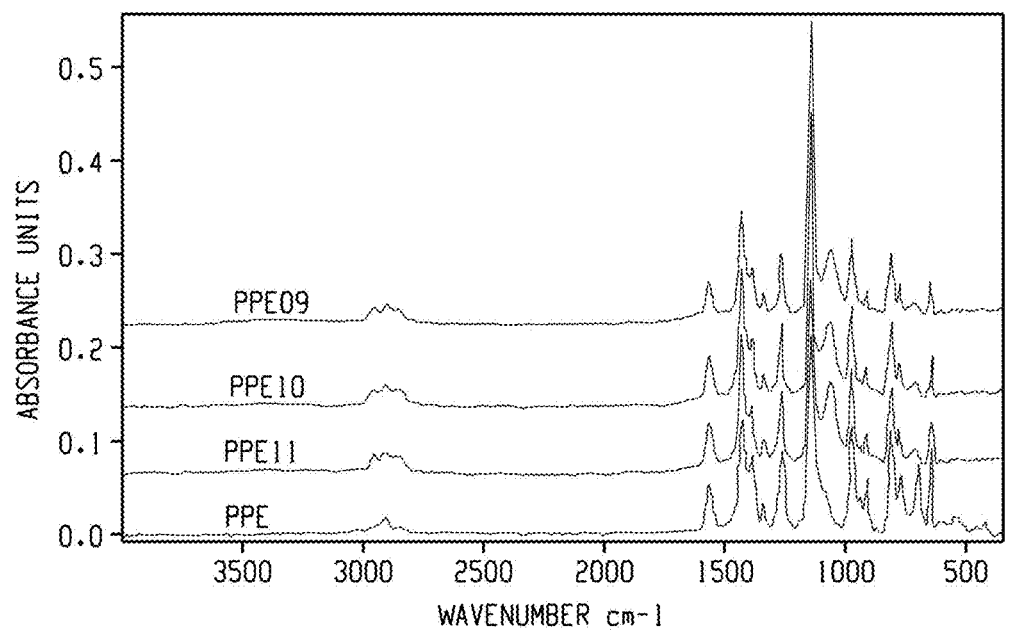
FIG. 3 depicts FTIR-ATIR spectra of the porous membranes of Examples 7-9 after soaking in water for 8 hours.

| Ex. | FIG. 3, 4 ID | Poloxamer | MPP-DMP Copoly. (wt. %) | Poloxamer (wt. %) | NMP (wt. %) | Viscosity at 20° C. (Pa · s) |
|---|---|---|---|---|---|---|
| Comp. 2 | PPE | None | 14.0 | 0 | 86.0 | — |
| 4 | PPE09 | L81 | 14.0 | 3.6 | 82.4 | 10.8 |
| 5 | PPE10 | 31R1 | 14.0 | 3.6 | 82.4 | 10.9 |
| 6 | PPE11 | P123 | 14.0 | 3.6 | 82.4 | 11.7 |

Figure 2:
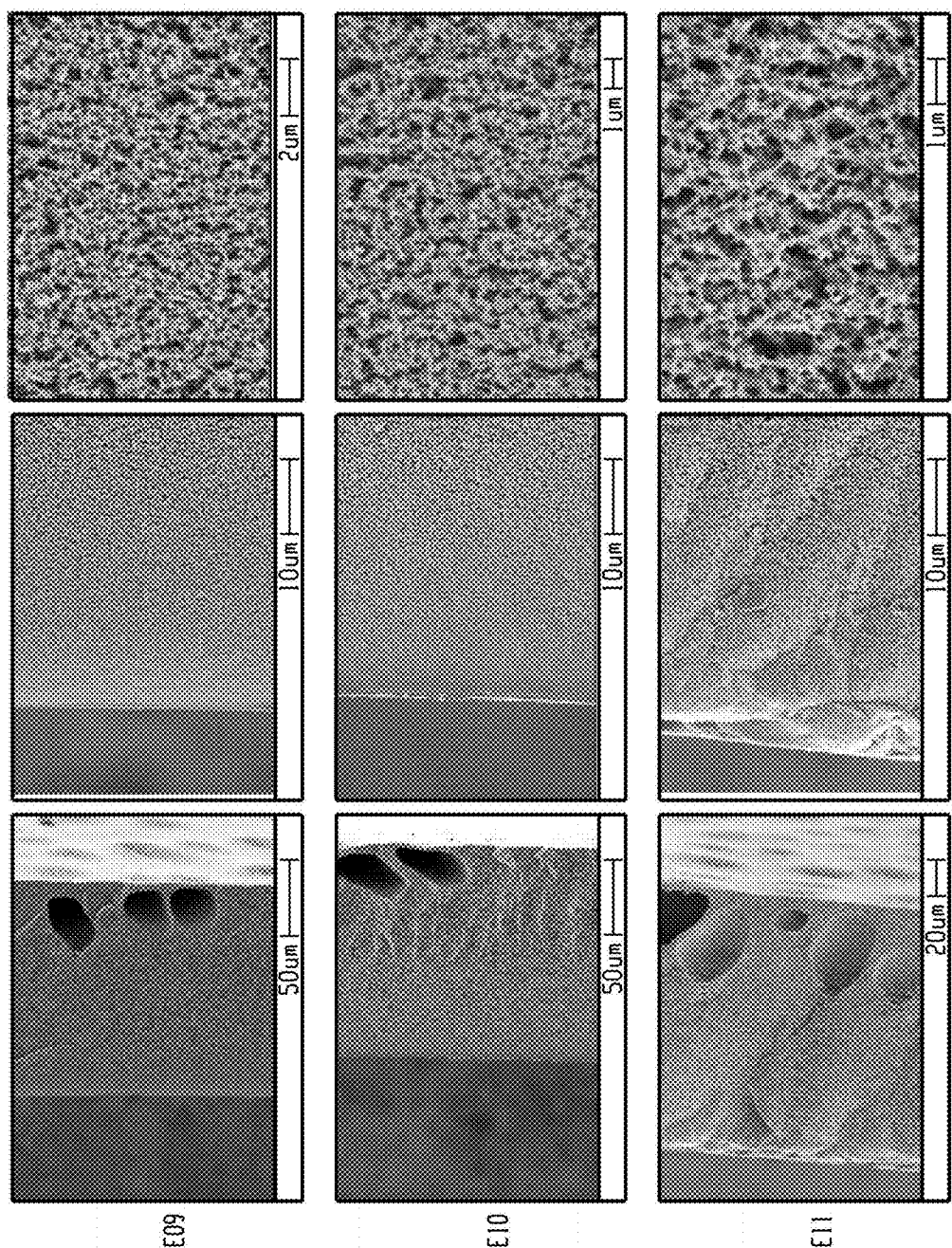
FIG. 2 depicts cross-sectional scanning electron microscopy (SEM) images of the porous membranes of Examples 7-9, composed of 20/80 MPP-DMP copolymer and poloxamers cast by phase-inversion in water.

Polymer films were cast from the dope solutions of Table 5 onto glass plates using a 0.3 μm depth casting knife. The films were subsequently submerged in a water bath at room temperature to form a flat sheet of porous membrane. The resulting porous membranes were soaked in fresh water for 8 hours to extract residual NMP solvent, and then dried in air. A JEOL JSM 6010LA Scanning Electron Microscope (SEM) was used for the initial characterization of the porous membrane morphology. The resulting SEM images are depicted in FIG. 2. As can be seen from FIG. 2, the porous membranes of Examples 4-6 all have an almost completely sponge-like structure with only a few macrovoids occurring at the bottom (glass plate) side of the porous membrane.

Figure 4:
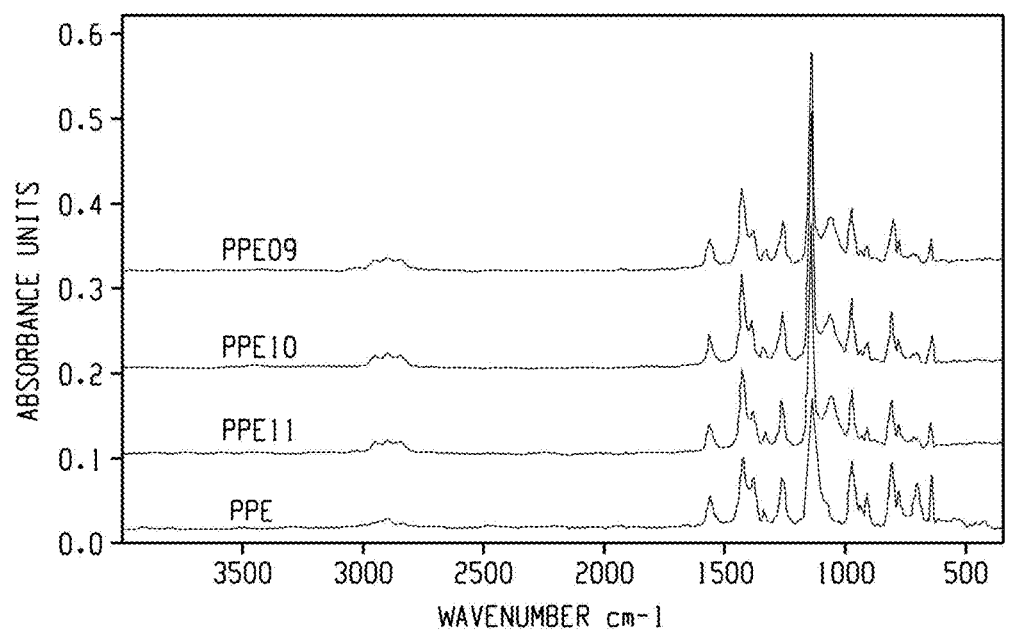
FIG. 4 depicts FTIR-ATIR spectra of the porous membranes of Examples 7-9 after an additional hour of sonication in water.

As can be seen from FIG. 3, analysis of the surfaces of the porous membranes of Examples 4-6 after drying by ATR-FTIR confirmed the presence of the poloxamers due to the increases in the intensity of the absorbance peak at 1110 cm$^{-1}$ relative to the MPP-DMP copolymer. The relative intensity of this absorbance relative to the other bands of the MPP-DMP copolymer of Comparative Example 2, appear to be very similar to the relative intensities shown in FIG. 1. This indicates that very little of the poloxamer has been lost to the aqueous coagulation bath. As a further test of the permanence of the poloxamers, the porous membranes of Examples 4-6 were sonicated an additional hour in water, dried and analyzed by ATR-FTIR again. The spectra are depicted in FIG. 4. The spectra are essentially unchanged from the corresponding spectra of FIG. 3. These data indicate that little or no poloxamer was extracted from the porous membranes, even after sonication in water for 1 hour. Without being bound by theory, it is thought that the PPO blocks of the poloxamers anchor the poloxamers to the MMP-DMP copolymer surface so that they are not extracted by water and sonication.

It is anticipated that improvements in the porous membranes can be obtained by optimization of the composition and molecular weight of the MPP-DMP copolymer, alone or in combination with optimization of the PEO content and number-average molecular weight of the poloxamer. It is also anticipated that suitable co-solvents such as glycerin can be useful in modifying the viscosity and cloud point of the membrane-forming compositions, and thereby the pore structures of the resulting porous membranes.

A desirable surface property for hollow fiber membranes to be used in applications such as renal dialysis is to be self-wetting. Assembled renal dialysis cartridges are shipped in a dry, sterile state to end-users such as clinics where they must be able to be rapidly re-wet and saturate the cartridges with saline solution with little or no applied pressure prior to being exposed to blood. This requirement provides a practical definition of self-wetting. The porous membranes of Examples 4-6 (Table 5) did not exhibit self-wetting behavior when a droplet of water was placed on their surfaces, even though the water contact angle data on dense films of the same compositions (Examples 1-3) suggested that they might be self-wetting.

Example 7: Porous Membrane with Increased Poloxamer Content

A series of porous membranes with increasing levels of P123 were prepared from the 20/80 MPP-DMP copolymer of Preparative Example 1. It was found that when the porous membrane was cast from a membrane-forming composition of 14 wt. % MPP-DMP copolymer, 10 wt. % P123, and 76 wt. % NMP (Example 11), the porous membrane spontaneously absorbed a droplet of water into the surface, and the water wicked across the surface.

Without being bound by theory, it is believed that a 1.4:1 weight ratio of MPP-DMP copolymer to P123 represents a threshold at which a sufficient amount of the PEO blocks of the poloxamer was able to migrate to the surface of the porous membrane during the rapid phase-inversion and coagulation, and so provide the desired hydrophilicity and self-wetting to the surface. This degree of hydrophilicity and self-wetting is comparable to that observed for the dense films cast from slowly-evaporating chloroform using a 4:1 weight ratio of MPP-DMP copolymer to P123 in Example 3.

Figure 5:
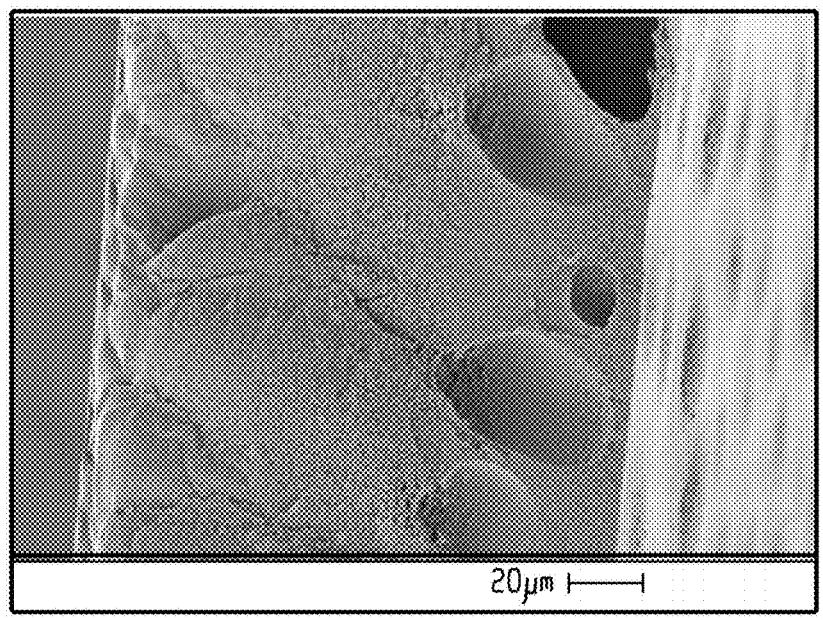
FIG. 5 depicts cross-sectional SEM images of the porous membranes of Examples 9 and 10, which illustrate the effect of increasing the amount of poloxamer P123 from 1:4 MPP-DMP copolymer to P123 to 1:1.4 MPP-DMP copolymer to P123 on membrane morphology.
Figure 5:
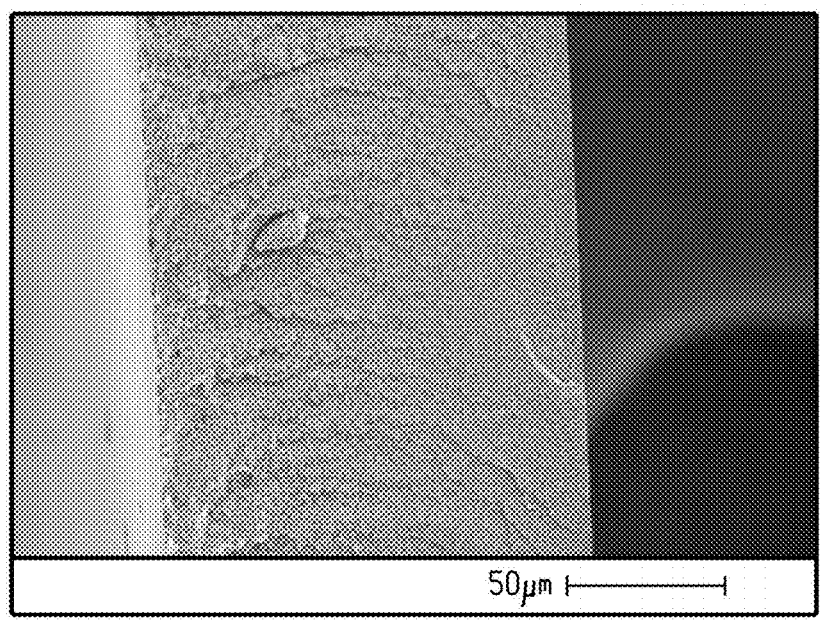

The cross-sectional morphology of the porous membranes of Examples 6 and 7 were studied by SEM. The SEM images are depicted in FIG. 5, where Example 6 is denoted "PPE12" and Example 7 is denoted "PPE15". The observed self-wetting behavior of Example 7 is associated with formation of a denser nanopore structure and little or no evidence of macrovoids in contrast to Example 6, which exhibits a less dense nanopore structure with several macrovoids. The morphology of Example 7 suggests that the porous membrane composition will be suitable for the formation of efficient hollow fiber membranes by coextrusion through an annular die. The morphology of Example 7 is also indicative of a favorable interaction between the MPP-DMP copolymer and P123.

The use of the terms "a" and "an" and "the" and similar referents in the context of describing the invention (especially in the context of the following claims) is to be construed to cover both the singular and the plural, unless otherwise indicated herein or clearly contradicted by context. "Or" means "and/or." The endpoints of all ranges directed to the same component or property are inclusive and independently combinable. Disclosure of a narrower range or more specific group in addition to a broader range is not a disclaimer of the broader range or larger group. All ranges disclosed herein are inclusive of the endpoints, and the endpoints are independently combinable with each other. The terms "first" and "second" and the like, as used herein do not denote any order, quantity, or importance, but are only used to distinguish one element from another. The term "comprises" as used herein is understood to encompass embodiments consisting essentially of, or consisting of, the named elements.

While typical embodiments have been set forth for the purpose of illustration, the foregoing descriptions should not be deemed to be a limitation on the scope herein. Accordingly, various modifications, adaptations, and alternatives can occur to one skilled in the art without departing from the spirit and scope herein.

The invention claimed is:

1. A separation module comprising a porous membrane comprising:
   a poly(phenylene ether) copolymer comprising 10 to 40 mole percent repeat units derived from 2-methyl-6-phenylphenol and 60 to 90 mole percent repeat units derived from 2,6-dimethylphenol; and
   a block copolymer comprising backbone or pendant blocks of poly($C_{2-4}$ alkylene oxide).

2. The separation module of claim 1, wherein the block copolymer is a poly(ethylene oxide)-poly(propylene oxide)-poly(ethylene oxide) block copolymer, a poly(ethylene oxide)-poly(propylene oxide)-poly(ethylene oxide) block copolymer, a poly($C_{2-4}$ alkylene oxide)-poly(dimethylsiloxane) block copolymer, or a combination comprising at least one of the foregoing.

3. The separation module of claim 1, wherein the porous membrane comprises 30 to 70 weight percent of the poly(phenylene ether) copolymer, and 30 to 70 weight percent of the block copolymer, based on the total weight of the porous membrane.

4. The separation module of claim 1, wherein the block copolymer comprises:
   a poly(ethylene oxide)-poly(propylene oxide)-poly(ethylene oxide) block copolymer having a number average molecular weight of 1,000 to 14,000 daltons, and comprising, based on the weight of the block copolymer, 1 to 90 weight percent, of poly(ethylene oxide) blocks;
   a poly(propylene oxide)-poly(ethylene oxide)-poly(propylene oxide) block copolymer having a number average molecular weight 500 to 12,000 daltons, and comprising, based on the weight of the block copolymer, 1 to 90 weight percent of poly(ethylene oxide) blocks; or
   a combination a combination comprising at least one of the foregoing.

5. The separation module of claim 4, wherein the poly(ethylene oxide)-poly(propylene oxide)-poly(ethylene oxide) block copolymer having a number average molecular weight of 1,000 to 14,000 daltons comprises, based on the weight of the block copolymer, 5 to 50 weight percent, of poly(ethylene oxide) blocks; and
   the poly(propylene oxide)-poly(ethylene oxide)-poly(propylene oxide) block copolymer having a number average molecular weight 500 to 12,000 daltons comprises, based on the weight of the block copolymer, 5 to 50 weight percent of poly(ethylene oxide) blocks.

6. The separation module of claim 1, wherein the block copolymer comprises a poly($C_{2-4}$ alkylene oxide)-poly(dimethylsiloxane) block copolymer comprising 5 to 60 weight percent polysiloxane, and having a number average molecular weight of 500 to 14,000 daltons.

7. The separation module of claim 1, wherein the porous membrane is a flat sheet.

8. The separation module of claim 7, wherein the flat sheet is in a spiral-wound configuration.

9. The separation module of claim 7, wherein the flat sheet is in a plate and frame configuration.

10. The separation module of claim 1, wherein the porous membrane is in a capillary or tubular configuration.

11. The separation module of claim 1, wherein the porous membrane is a hollow fiber.

12. The separation module of claim 11, wherein the separation module comprises:
    an enclosure configured to contain a bundle of the hollow fibers, the enclosure having an outlet configured for withdrawing a permeate fluid;
    a first encasement comprising a thermoset or a thermoplastic polymeric material and located at a first end of the bundle, arranged such that the hollow fiber membranes are embedded in the first encasement and communicate through the first encasement and are open on an outer face of the first encasement;
    a second encasement comprising a thermoset or a thermoplastic polymeric material and located at a second end of the bundle opposite the first end of the bundle, arranged such that the hollow fiber membranes are embedded in the second encasement and communicate through the second encasement and are open on an outer face of the second encasement;
    a first end cap arranged and configured for attaching and sealing to the first end of the bundle or enclosures at the first encasement;
    a second end cap arranged and configured for attaching and sealing to the second end of the bundle or enclosures at the second encasement;
    an inlet for introducing a fluid mixture to be separated into bores of the hollow fiber membranes at the first encasement; and
    an outlet for withdrawing a retentate fluid from the bores for the hollow fiber membranes at the second encasement.

13. A device for wastewater treatment, water purification, desalination, or separating water-insoluble oil from oil-containing wastewater, the device comprising the separation module of claim 1.

14. A device for purification of a liquid by membrane distillation comprising the separation module of claim 1.

15. A device for sugar purification, protein concentration, or enzyme recovery, comprising the separation module of claim 1.

16. A dialysis device for conducting hemodialysis on a patient suffering from renal failure, the device comprising the separation module of claim 11.

17. A dialysis device for conducting liver dialysis on a patient suffering from liver failure, the device comprising the separation module of claim 11.

18. A blood oxygenator comprising the separation module of claim 11.

19. A system comprising:
a server;
the dialysis device of claim 16 configured to connect to the server through a network; and
a client device also configured to connect to the server through the network,
wherein the server is configured for:
maintaining an access control list to determine whether the client device is authorized to connect to the device; and
providing a connection for transfer of data between the dialysis device and the client device.

20. The system of claim 19, wherein the server is further configured for:
receiving a request for a network connection from the dialysis device;
establishing the network connection with the dialysis device;
receiving, from the client device, a request to access the dialysis device;
authorizing the client device to access the dialysis device;
receiving from the dialysis device information pertaining to operation of the dialysis device; and
providing to the client device the information.

21. The system of claim 19, wherein the dialysis device and client device are at a first location, and the server is at a remote location relative to the first location.

22. The separation module of claim 1, wherein the poly (phenylene ether) copolymer has a weight average molecular weight of 75,000 to 300,000 daltons, as measured by gel permeation chromatography against polystyrene standards.

23. The separation module of claim 1, wherein the porous membrane comprises 30 to 60 weight percent of the poly (phenylene ether) copolymer, and 40 to 70 weight percent of the block copolymer, based on the total weight of the porous membrane.

24. The separation module of claim 1, wherein the poly (phenylene ether) copolymer consists of 10 to 30 mole percent 2-methyl-6-phenylphenol and 70 to 90 mole percent 2,6-dimethylphenol.

25. The separation module of claim 1, wherein the weight average molecular weight of the poly(phenylene ether) copolymer is greater than or equal to 100,000 daltons and less than or equal to 300,000 daltons.

\* \* \* \* \*